(12) United States Patent
Howland

(10) Patent No.: US 6,770,075 B2
(45) Date of Patent: Aug. 3, 2004

(54) SPINAL FIXATION APPARATUS WITH ENHANCED AXIAL SUPPORT AND METHODS FOR USE

(76) Inventor: Robert S. Howland, 560 Old Ranch Rd., Seal Beach, CA (US) 90740

(*) Notice: Subject to any disclaimer, the term of this patent is extended or adjusted under 35 U.S.C. 154(b) by 0 days.

(21) Appl. No.: 10/133,310

(22) Filed: Apr. 24, 2002

(65) Prior Publication Data
US 2002/0173791 A1 Nov. 21, 2002

Related U.S. Application Data

(63) Continuation-in-part of application No. 09/861,278, filed on May 17, 2001.

(51) Int. Cl.[7] .............................................. A61B 17/56
(52) U.S. Cl. .................................... 606/61; 606/73
(58) Field of Search ............................. 606/61, 60, 72, 606/73, 53, 54, 105, 57, 58

(56) References Cited

U.S. PATENT DOCUMENTS

| | | |
|---|---|---|
| 2,696,817 A | 12/1954 | Prevo |
| 3,997,138 A | 12/1976 | Crock et al. |
| 4,599,086 A | 7/1986 | Doty |
| 4,648,388 A | 3/1987 | Steffee |
| 4,653,481 A | 3/1987 | Howland et al. |
| 4,719,905 A | 1/1988 | Steffee |
| 4,743,256 A | 5/1988 | Brantigan |
| 4,771,767 A | 9/1988 | Steffee |
| 4,805,602 A | 2/1989 | Puno et al. |
| 4,815,453 A | 3/1989 | Cotrel |
| 4,820,305 A | 4/1989 | Harms et al. |
| 4,827,918 A | 5/1989 | Olerud |
| 4,836,193 A | 6/1989 | Ransford |
| 4,854,304 A | 8/1989 | Zielke |
| 4,854,311 A | 8/1989 | Steffee |
| 4,863,476 A | 9/1989 | Shepperd |
| 4,887,596 A | 12/1989 | Sherman |
| 4,892,545 A | 1/1990 | Day et al. |
| 4,931,055 A | 6/1990 | Bumpus et al. |
| 4,932,975 A | 6/1990 | Main et al. |
| 4,944,743 A | 7/1990 | Gotzen et al. |
| 4,946,458 A | 8/1990 | Harms et al. |
| 4,950,270 A | 8/1990 | Bowman et al. |
| 4,963,144 A | 10/1990 | Huene |
| 4,987,892 A | 1/1991 | Krag et al. |
| 4,998,936 A | 3/1991 | Mehdian |
| 5,000,165 A | 3/1991 | Watanabe |
| 5,000,166 A | 3/1991 | Karpf |

(List continued on next page.)

OTHER PUBLICATIONS

Centerpulse Spine–Tech Website pages on the ST360°™ Spinal Fixation System (http://www.centerpulsespinetech-.com/spine/products/lumbar/st360/index).

(List continued on next page.)

Primary Examiner—Pedro Philogene
(74) Attorney, Agent, or Firm—Orrick, Herrington & Sutcliffe, LLP

(57) ABSTRACT

A spinal fixation system includes a plurality of anchor screw assemblies, e.g. including anchor screws and clamp assemblies defining rod passages therethrough. A rod is receivable in the rod passages between the anchor screw assemblies, and a spacer is securable on the rod. During use, a first anchor screw is screwed into a first vertebra, and a second anchor screw is screwed into a second vertebra adjacent the first vertebra, and clamp assemblies are mounted to each anchor screw. A rod is secured between the anchor screw assemblies, thereby fixing a relative spacing of the first and second vertebrae. A spacer is crimped onto the exposed portion of the rod between the anchor screw assemblies, the spacer extending between the anchor screw assemblies to prevent the anchor screw assemblies, and, consequently, the first and second vertebrae, from moving towards one another.

21 Claims, 11 Drawing Sheets

U.S. PATENT DOCUMENTS

| | | |
|---|---|---|
| 5,002,542 A | 3/1991 | Frigg |
| 5,005,562 A | 4/1991 | Cotrel |
| 5,007,909 A | 4/1991 | Rogozinski |
| 5,010,879 A | 4/1991 | Moriya et al. |
| 5,011,484 A | 4/1991 | Bréard |
| 5,015,247 A | 5/1991 | Michelson |
| 5,030,220 A | 7/1991 | Howland |
| 5,034,011 A | 7/1991 | Howland |
| 5,041,113 A | 8/1991 | Biedermann et al. |
| 5,042,982 A | 8/1991 | Harms et al. |
| 5,047,029 A | 9/1991 | Aebi et al. |
| 5,053,034 A | 10/1991 | Olerud |
| 5,057,109 A | 10/1991 | Olerud |
| 5,062,850 A | 11/1991 | MacMillan et al. |
| 5,067,955 A | 11/1991 | Cotrel |
| 5,067,956 A | 11/1991 | Buford, III et al. |
| 5,084,048 A * | 1/1992 | Jacob et al. .................. 606/61 |
| 5,084,049 A | 1/1992 | Asher et al. |
| 5,084,050 A | 1/1992 | Draenert |
| 5,085,660 A | 2/1992 | Lin |
| 5,092,866 A | 3/1992 | Breard et al. |
| 5,092,867 A | 3/1992 | Harms et al. |
| 5,092,893 A | 3/1992 | Smith |
| 5,098,434 A | 3/1992 | Serbousek |
| 5,108,395 A | 4/1992 | Laurain |
| 5,108,438 A | 4/1992 | Stone |
| 5,112,332 A | 5/1992 | Cozad et al. |
| 5,120,171 A | 6/1992 | Lasner |
| 5,122,131 A | 6/1992 | Tsou |
| 5,127,912 A | 7/1992 | Ray et al. |
| 5,129,388 A | 7/1992 | Vignaud et al. |
| 5,129,899 A | 7/1992 | Small et al. |
| 5,129,900 A | 7/1992 | Asher et al. |
| 5,129,901 A | 7/1992 | Decoste |
| 5,133,716 A | 7/1992 | Plaza |
| 5,133,717 A | 7/1992 | Chopin |
| 5,147,359 A | 9/1992 | Cozad et al. |
| 5,147,360 A | 9/1992 | Dubousset |
| 5,147,361 A | 9/1992 | Ojima et al. |
| 5,147,362 A | 9/1992 | Goble |
| 5,147,363 A | 9/1992 | Härle |
| 5,147,402 A | 9/1992 | Bohler et al. |
| 5,147,404 A | 9/1992 | Downey |
| 5,151,103 A | 9/1992 | Tepic et al. |
| 5,152,303 A | 10/1992 | Allen |
| 5,154,718 A | 10/1992 | Cozad et al. |
| 5,154,719 A | 10/1992 | Cotrel |
| 5,167,662 A | 12/1992 | Hayes et al. |
| 5,167,664 A | 12/1992 | Hodorek |
| 5,169,400 A | 12/1992 | Mühling et al. |
| 5,171,278 A | 12/1992 | Pisharodi |
| 5,171,279 A | 12/1992 | Mathews |
| 5,171,280 A | 12/1992 | Baumgartner |
| 5,171,281 A | 12/1992 | Parsons et al. |
| 5,176,678 A | 1/1993 | Tsou |
| 5,176,679 A | 1/1993 | Lin |
| 5,176,680 A | 1/1993 | Vignaud et al. |
| 5,180,381 A | 1/1993 | Aust et al. |
| 5,180,382 A | 1/1993 | Frigg et al. |
| 5,180,388 A | 1/1993 | DiCarlo |
| 5,180,393 A | 1/1993 | Commarmond |
| 5,181,917 A | 1/1993 | Rogozinski |
| 5,190,543 A | 3/1993 | Schläpfer |
| 5,196,013 A | 3/1993 | Harms et al. |
| 5,196,014 A | 3/1993 | Lin |
| 5,196,015 A | 3/1993 | Neubardt |
| 5,201,734 A | 4/1993 | Cozad et al. |
| 5,207,678 A | 5/1993 | Harms et al. |
| 5,209,751 A | 5/1993 | Farris et al. |
| 5,209,752 A | 5/1993 | Ashman et al. |
| 5,209,753 A | 5/1993 | Biedermann et al. |
| 5,217,461 A | 6/1993 | Asher et al. |
| 5,217,462 A | 6/1993 | Asnis et al. |
| 5,217,497 A | 6/1993 | Mehdian |
| 5,222,954 A | 6/1993 | Baker et al. |
| 5,226,766 A | 7/1993 | Lasner |
| 5,226,906 A | 7/1993 | Crombie et al. |
| 5,234,430 A | 8/1993 | Huebner |
| 5,234,431 A | 8/1993 | Keller |
| 5,236,431 A | 8/1993 | Gogolewski et al. |
| 5,236,460 A | 8/1993 | Barber |
| 5,242,443 A | 9/1993 | Kambin |
| 5,242,444 A | 9/1993 | MacMillan |
| 5,242,445 A | 9/1993 | Ashman |
| 5,242,446 A | 9/1993 | Steffee et al. |
| 5,242,447 A | 9/1993 | Borzone |
| 5,246,442 A | 9/1993 | Ashman et al. |
| 5,246,458 A | 9/1993 | Graham |
| 5,247,994 A | 9/1993 | Nenniger |
| 5,254,118 A | 10/1993 | Mirkovic |
| 5,257,993 A | 11/1993 | Asher et al. |
| 5,257,994 A | 11/1993 | Lin |
| 5,258,031 A | 11/1993 | Salib et al. |
| 5,259,398 A | 11/1993 | Vrespa |
| 5,261,909 A * | 11/1993 | Sutterlin et al. ............... 606/61 |
| 5,267,999 A | 12/1993 | Olerud |
| 5,275,600 A | 1/1994 | Allard et al. |
| 5,281,222 A | 1/1994 | Allard et al. |
| 5,281,223 A | 1/1994 | Ray |
| 5,282,862 A | 2/1994 | Baker et al. |
| 5,282,863 A | 2/1994 | Burton |
| 5,290,288 A | 3/1994 | Vignaud et al. |
| 5,290,289 A | 3/1994 | Sanders et al. |
| 5,300,073 A | 4/1994 | Ray et al. |
| 5,304,178 A | 4/1994 | Stahurski |
| 5,304,179 A | 4/1994 | Wagner |
| 5,304,210 A | 4/1994 | Crook |
| 5,306,275 A | 4/1994 | Bryan |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,306,311 A | 4/1994 | Stone et al. |
| 5,312,404 A | 5/1994 | Asher et al. |
| 5,312,405 A | 5/1994 | Korotko et al. |
| 5,330,473 A | 7/1994 | Howland |
| 5,360,429 A | 11/1994 | Jeanson et al. |
| 5,360,431 A | 11/1994 | Puno et al. |
| 5,360,448 A | 11/1994 | Thramann |
| 5,364,399 A | 11/1994 | Lowery et al. |
| 5,364,400 A | 11/1994 | Rego, Jr. et al. |
| 5,366,455 A | 11/1994 | Dove et al. |
| 5,368,593 A | 11/1994 | Stark |
| 5,368,594 A | 11/1994 | Martin et al. |
| 5,374,267 A | 12/1994 | Siegal |
| 5,380,323 A * | 1/1995 | Howland ..................... 606/61 |
| 5,380,324 A | 1/1995 | Müller et al. |
| 5,380,325 A | 1/1995 | Lahille et al. |
| 5,380,326 A | 1/1995 | Lin |
| 5,380,327 A | 1/1995 | Eggers et al. |
| 5,382,248 A | 1/1995 | Jacobson et al. |
| 5,385,565 A | 1/1995 | Ray |
| 5,385,583 A | 1/1995 | Cotrel |
| 5,387,212 A | 2/1995 | Yuan et al. |
| 5,387,213 A | 2/1995 | Breard et al. |
| RE34,985 E | 6/1995 | Pennig |
| 5,423,816 A | 6/1995 | Lin |
| 5,423,818 A | 6/1995 | Van Hoeck et al. |
| 5,425,732 A | 6/1995 | Ulrich |
| 5,429,639 A | 7/1995 | Judet |
| 5,437,669 A | 8/1995 | Yuan et al. |

| | | |
|---|---|---|
| 5,437,670 A | 8/1995 | Sherman et al. |
| 5,437,671 A | 8/1995 | Lozier et al. |
| 5,443,467 A | 8/1995 | Biedermann et al. |
| 5,466,237 A | 11/1995 | Byrd, III et al. |
| 5,474,555 A | 12/1995 | Puno et al. |
| 5,487,744 A * | 1/1996 | Howland ............ 606/61 |
| 5,496,318 A | 3/1996 | Howland et al. |
| 5,545,164 A * | 8/1996 | Howland ............ 606/61 |
| 5,545,166 A | 8/1996 | Howland |
| 5,549,608 A | 8/1996 | Errico et al. |
| 5,554,157 A | 9/1996 | Errico et al. |
| 5,562,660 A * | 10/1996 | Grob ............ 606/61 |
| 5,584,834 A | 12/1996 | Errico et al. |
| 5,586,984 A | 12/1996 | Errico et al. |
| 5,628,740 A | 5/1997 | Mullane |
| 5,647,873 A | 7/1997 | Errico et al. |
| 5,669,911 A | 9/1997 | Errico et al. |
| 5,672,176 A | 9/1997 | Biedermann et al. |
| 5,690,630 A | 11/1997 | Errico et al. |
| 5,716,357 A | 2/1998 | Rogozinski |
| 5,725,528 A | 3/1998 | Errico et al. |
| 5,728,098 A | 3/1998 | Sherman et al. |
| 5,733,284 A * | 3/1998 | Martin ............ 606/61 |
| 5,733,286 A | 3/1998 | Errico et al. |
| 5,735,850 A | 4/1998 | Baumgartner et al. |
| 5,735,851 A | 4/1998 | Errico et al. |
| 5,752,957 A | 5/1998 | Ralph et al. |
| 5,776,135 A | 7/1998 | Errico et al. |
| 5,782,833 A | 7/1998 | Haider |
| 5,800,435 A | 9/1998 | Errico et al. |
| 5,810,819 A | 9/1998 | Errico et al. |
| 5,814,046 A | 9/1998 | Hopf |
| 5,817,094 A | 10/1998 | Errico et al. |
| 5,882,350 A | 3/1999 | Ralph et al. |
| 5,910,142 A | 6/1999 | Tatar |
| 5,928,232 A * | 7/1999 | Howland et al. ............ 606/61 |
| 5,954,725 A | 9/1999 | Sherman et al. |
| 5,964,760 A | 10/1999 | Richelsoph |
| 5,980,523 A | 11/1999 | Jackson |
| 5,997,539 A | 12/1999 | Errico et al. |
| 6,010,504 A | 1/2000 | Rogozinski |
| 6,015,409 A * | 1/2000 | Jackson ............ 606/61 |
| 6,019,759 A | 2/2000 | Rogozinski |
| 6,063,089 A | 5/2000 | Errico et al. |
| 6,083,226 A | 7/2000 | Fiz |
| 6,113,601 A | 9/2000 | Tatar |
| 6,132,434 A | 10/2000 | Sherman et al. |
| 6,261,287 B1 | 7/2001 | Metz-Stavenhagen |
| 6,280,442 B1 | 8/2001 | Barker et al. |
| 6,287,311 B1 | 9/2001 | Sherman et al. |
| 6,309,391 B1 * | 10/2001 | Crandall et al. ............ 606/61 |
| RE37,665 E | 4/2002 | Ralph et al. |
| 6,379,354 B1 | 4/2002 | Rogozinski |
| 6,451,021 B1 | 9/2002 | Ralph et al. |
| 6,454,773 B1 | 9/2002 | Sherman et al. |
| 6,471,705 B1 | 10/2002 | Biedermann et al. |
| 6,478,798 B1 | 11/2002 | Howland |
| 6,537,276 B2 | 3/2003 | Metz-Stavenhagen |
| 6,562,040 B1 | 5/2003 | Wagner |
| 6,565,567 B1 | 5/2003 | Haider |
| 6,595,992 B1 | 7/2003 | Wagner et al. |

OTHER PUBLICATIONS

Centerpulse Spine–Tech Website pages on the Silhouette™ product (http://www.centerpulsespinetech.com/spine/products/lumbar/silhouette/index).

Centerpulse Spine–Tech Website pages on the Optima™Spinal Fixation System (http://www.centerpulsespinetech.com/spine/products/lumbar/optima/index).

Centerpulse Spine–Tech Website pages on the DYNESYS® The Dynamic Stabilization System (http://www.centerpulsespinetech.com/spine/products/lumbar/dynesys/index).

Medtronic Sofamor Danek Website pages on the TSRH® Spinal System (http://www.sofamordanek.com/stripcontent.php?parent_file=/physician–spinal–trsh.htm...).

Medtronic Sofamor Danek Website pages on the CD HORIZON® Spinal System (http://www.sofamordanek.com/stripcontent.php?parent_file=/physician–spinal–spinal.htm. . .).

Medtronic Sofamor Danek Website pages on the CD HORIZON® M8 and M10 Spinal Systems (http://www.sofamordanek.com/stripcontent.php?parent_file=/physician–spinal–fas.html&. . . ).

Medtronic Sofamor Danek Website pages on the CD HORIZON® M8 and M10 Multi Axial Screw Spinal Systems (http://www.sofamordanek.com/stripcontent.php? parent_file=/physician–spinal–mas.html...).

Medtronic Sofamor Danek Website pages on the COLORADO 2™ Spinal System (http://www.sofamordanek.com/stripcontent.php?parent_file=/physician–spinal–colorado.h...).

Medtronic Sofamor Danek Website pages on the TSRH–3D® Vertebral Body Reduction Spinal Instrumentation (http://www.sofamordanek.com/stripcontent.php?parent_file=/physician–spinal–trshvbr.ht...).

May 12, 2003 Press Release form Aesculap Website entitled "Aesculap announces agreement with spinal innovations for SHADOW™ pedicle screw system" (http://www.aesculap-usa.com/aboutus/in_news/ab_in_news13.htmo), 1999–2002.

Aesculap Website pages on its Cranio Spine Business unit (http://www.aesculap–usa.com/produkt_service/cranio_bu/ps_cbu.htm), 1999–2002.

Synthes–Stratec Website page on its spine portfolio (http://www.synthes-stratec.com/html/4322.98.html), 2003.

Synthes AG Chur Website page (http://www.syntheschur.ch/), Feb. 18, 2003.

EBI Medical Website pages on the VueLock® Anterior Cervical Plate System (http://www.ebimedical.com/products/spine/vuelock.html), 2002.

EBI Medical Website page on the Ionic ™ Spine Spacer System (http://www.ebimedical.com/products/spine/ionic.html), 2003.

EBI Medical Website pages on the Ω mega21™ Expandable Screw for Spine Fixation (http://www.ebimedical.com/products/spine/expandable.html), 2002.

EBI Medical Website pages on the Ω mega21™ Versatile Rod System (http://www.ebimedical.com/products/spine/omega.html), 2002.

EBI Medical Website pages on the SpineLink® Anterior Cervical Spinal System (http://www.ebimedical.com/products/spine/anterior.html), 2002.

EBI Medical Website pages on the SpineLink®–II The Next Generation in Independent Intrasegmental Fixation (http://www.ebimedical.com/products/spine/spinelink2.html), 2003.

EBI Medical Website pages on the SpineLink® The Independent Intrasegmental Solution to Spine Fixation (http://www.ebimedical.com/products/spine/spinelink.html), 2002.

Interpore Cross International Website pages on the Altius™ System Occipito–Cervico–Thoracic Posterior Spinal Fixation (http://www.interpore.com/product_altius.html), 2003.

Interpore Cross International Website pages on the C–TEK® Anterior Cervical Plate System (http://www.interpore.com/product_ctek.html), 2003.

Interpore Cross International Website pages on the SYNERGY™ Spinal System (http://www.interpore.com/product_synergy.html), 2003.

Interpore Cross International Website pages on the SYNERGY™ IQ Low Back System (http://www.interpore.com/product_synergy_q.html), 2003.

Interpore Cross International Website pages on the SYNERGY™ Deformity System (http://www.interpore.com/product_synergy_ds.html), 2003.

Interpore Cross Internaitonal Website pages on the TPS198 C The Telescopic Plate Spacer for Cervical Spine (http://www.interpore.com/product_tps.html), 2003.

Interpore Cross International Website pages on the TPS™–TL The Telescopic Plate Spacer for Thoracolumbar Spine (http://www.interpore.com/product_tps_tl.html), 2003.

DePuy Spine, Inc. Website pages on the SUMMIT™ Channel Plate Fixation System (http://www.depuyacromed.com/products/other/summit_channel.asp), 2003.

DePuy Spine, Inc. Website pages on the SUMMIT™ 3.0 MM Rod Fixation System (http://www.depuyacromed.com/products/other/summit_rod.asp), 2003.

DePuy Spine, Inc. Website pages on the SUMMIT™ SI Spinal Fixation System (http://www.depuyacromed.com/products/cervical/summit_si_oct.asp), 2003.

DePuy Spine, Inc. Website pages on the DOC™ Rod (http://www.depuyacromed.com/products/cervical/docrod.asp), 2003.

DePuy Spine, Inc. Website pages on the ISOLA®/VSP® Spine System (http://www.depuyacromed.com/products/deformity/isola.asp), 2003.

DePuy Spine, Inc. Website pages on the TiMX™ Comprehensive Low Back System (http://www.depuyacromed.com/products/deformity/timx_comprehensive.asp), 2003.

DePuy Spine, Inc. Website pages on the MOSS MIAMI™ 4.0 (Small Stature Patients) (http://www.depuyacromed.com/products/deformity/moss_miami40.asp), 2003.

DePuy Spine, Inc. Website pages on the MOSS MIAMI SI™ (http://www.depuyacromed.com/products/deformity/moss_miami_si.asp), 2003.

DePuy Spine, Inc. Website pages on the MOSS MIAMI™ 5.5 Ti (http://www.depuyacromed.com/products/deformity/moss_miami55.asp), 2003.

DePuy Spine, Inc. Website pages on the MOSS MIAMI™ 5.0 SS (http://www.depuyacromed.com/products/deformity/moss_miami50.asp), 2003.

DePuy Spine, Inc. Website pages on the MONARCH™ 5.5 Ti (http://www.depuyacromed.com/products/deformity/monarch55.asp), 2003.

DePuy Spine, Inc. Website pages on the FRONTIER™ (http://www.depuyacromed.com/products/deformity/frontier.asp), 2003.

DePuy Spine, Inc. Website pages on the CROSSOVER™ (http://www.depuyacromed.com/products/deformity/cross.asp), 2003.

DePuy Spine, Inc. Website pages on the MODULAR CROSS CONNECTOR™ (MCC) (http://www.depuyacromed.com/products/deformity/modular_cross.asp), 2003.

DePuy Spine, Inc. Website pages on the MONARCH™ 6.35 Ti (http://www.depuyacromed.com/products/deformity/monarch.html), 2002.

DePuy Spine, Inc. Website pages on the UNIVERSITY PLATE™ System (http://www.depuyacromed.com/products/trauma/university_plate.asp), 2003.

DePuy Spine, Inc. Website pages on the PEAK™ Polyaxial Anterior Cervical Plate (http://www.depuyacromed.com/products/cervical/peak_polyaxial.asp), 2003.

DePuy Spine, Inc. Website pages on the DOC™ Plate (http://www.depuyacromed.com/products/cervical/doc-plate.asp), 2003.

Stryker Corporation Website page on the Stryker Spine Implants (http://www.strykercorp.com/products/spine.htm).

* cited by examiner

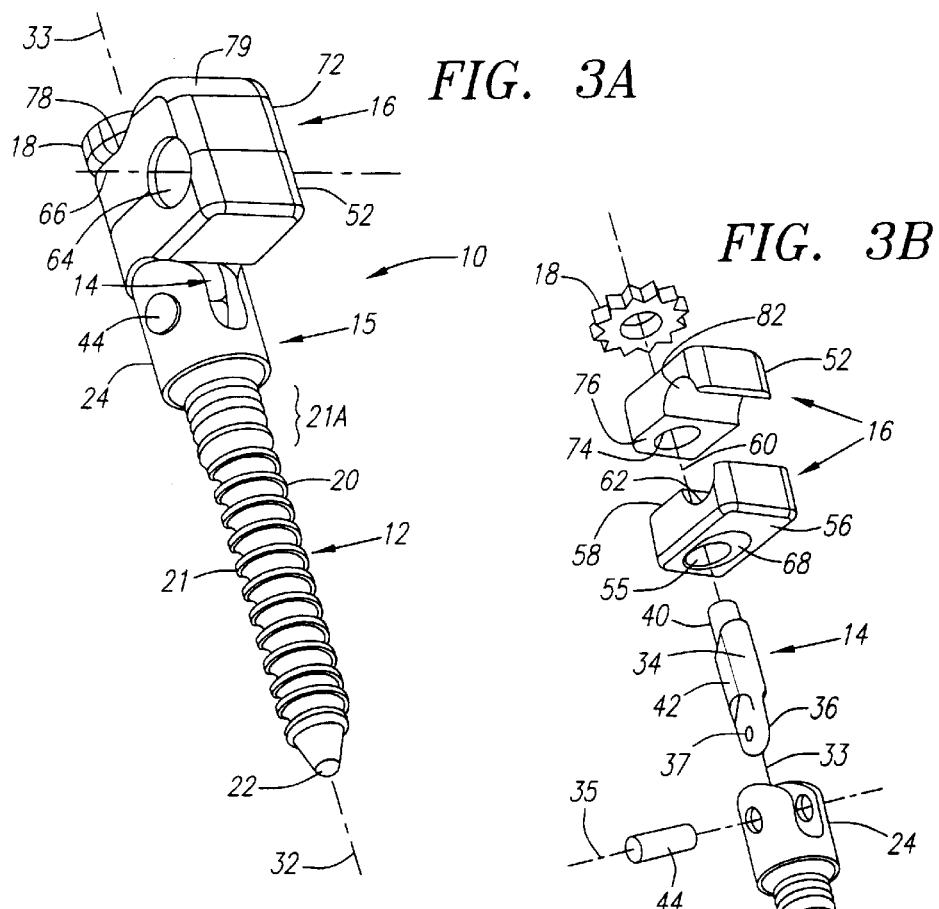
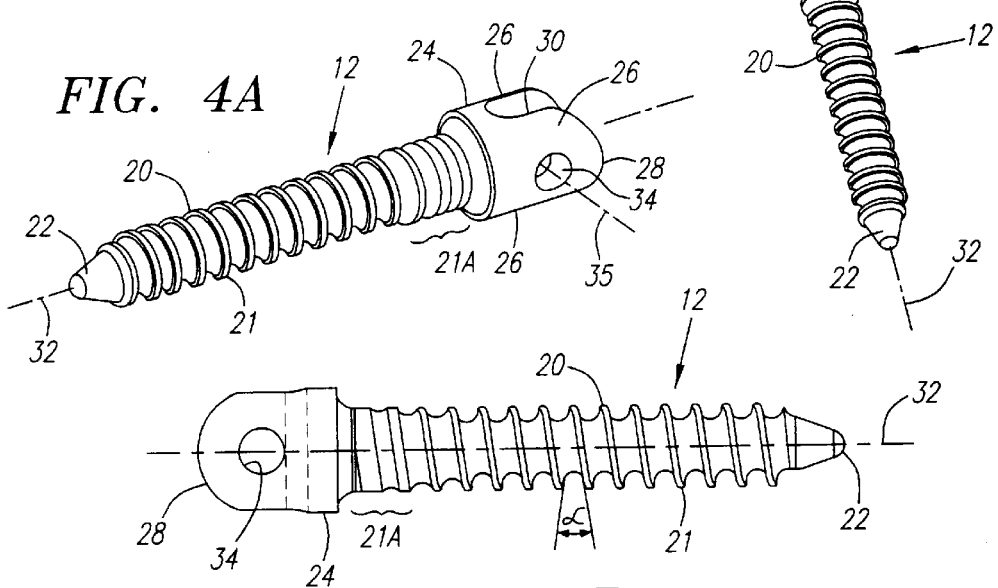

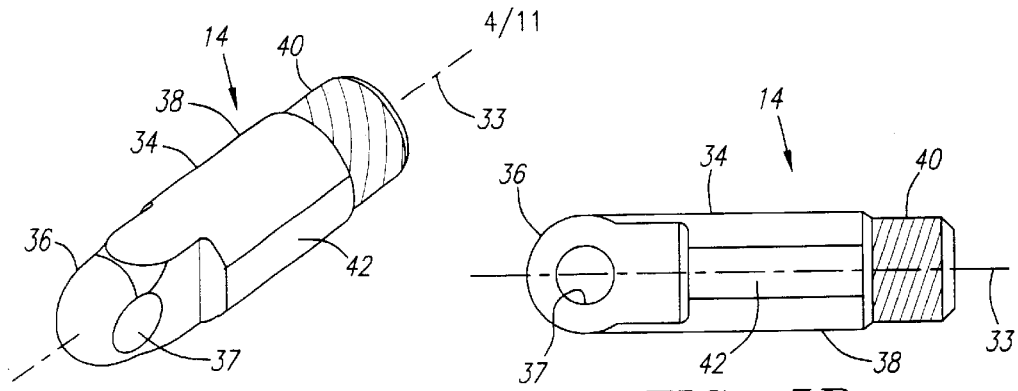
FIG. 5A  FIG. 5B
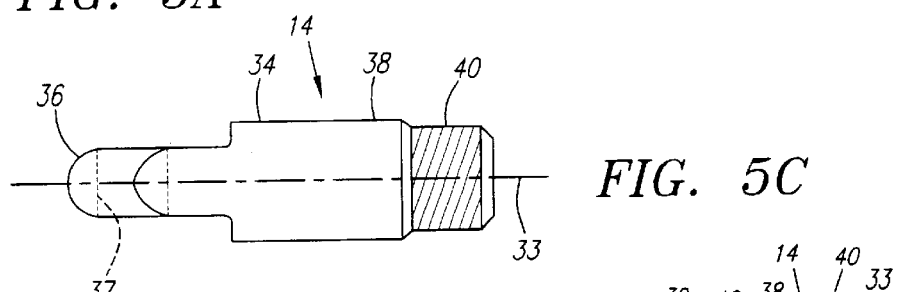
FIG. 5C
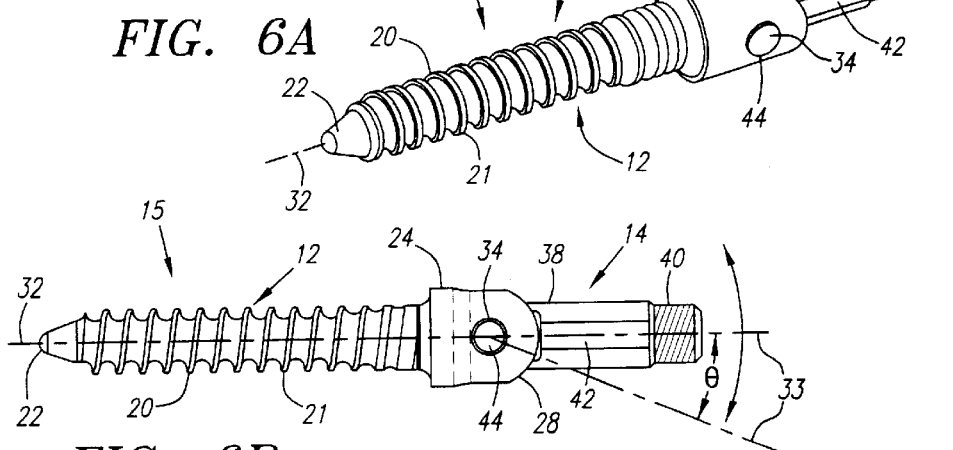
FIG. 6A
FIG. 6B
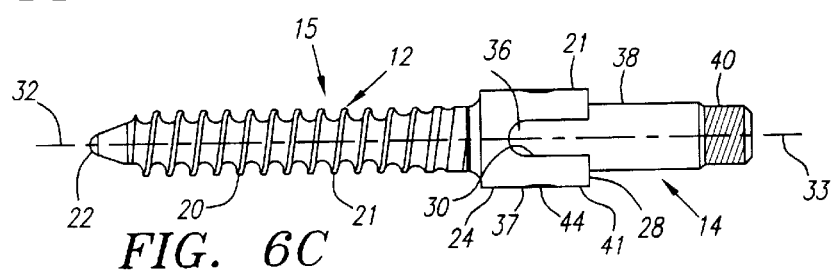
FIG. 6C

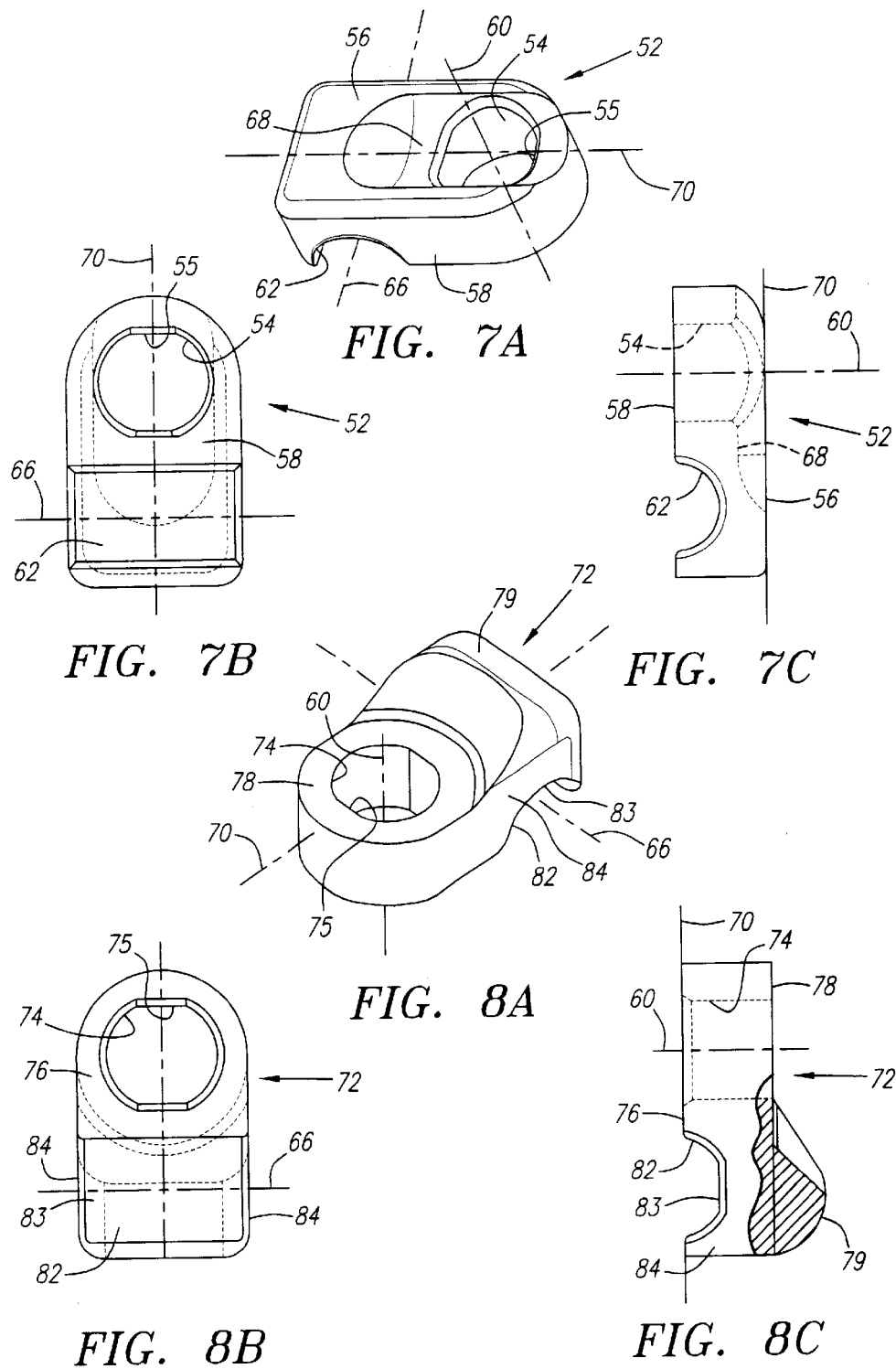

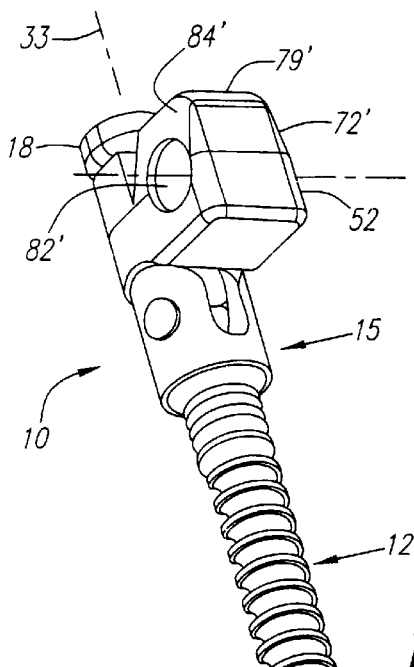
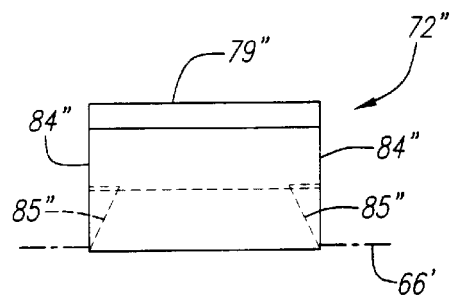
FIG. 15C
FIG. 14
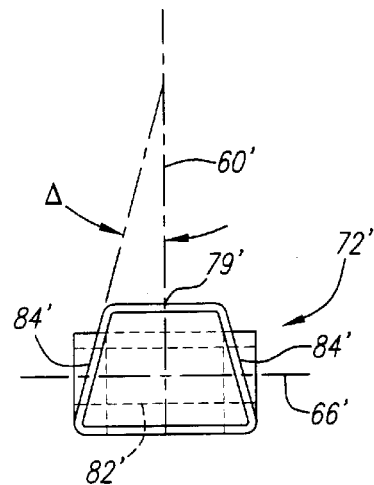
FIG. 15B
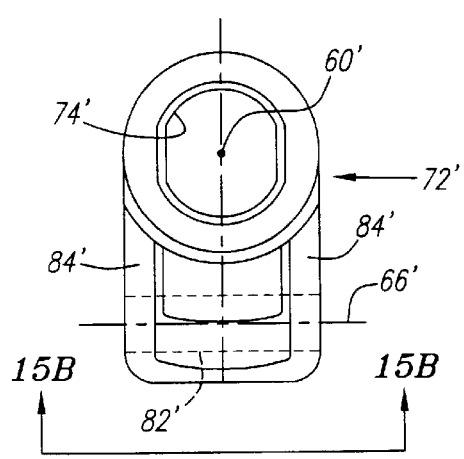
FIG. 15A

SPINAL FIXATION APPARATUS WITH ENHANCED AXIAL SUPPORT AND METHODS FOR USE

This application is a continuation-in-part of application Ser. No. 09/861,278, filed May 17, 2001, the disclosure of which is expressly incorporated herein by reference.

FIELD OF THE INVENTION

The present invention relates generally to apparatus and methods for treating spinal disorders, and more particularly to spinal fixation systems that may be secured between adjacent anchor screw assemblies, and methods for stabilizing, adjusting, or otherwise fixing adjacent vertebrae using such spinal fixation systems.

BACKGROUND

Various systems and methods have been suggested for treating spinal disorders, such as degenerative discs, stenosis, trauma, scoliosis, kyphosis, or spondylolisthesis. For example, U.S. Pat. No. 5,545,166, naming the same inventor as the present application, discloses a spinal fixation system that includes a plurality of anchor screws, clamp assemblies, pivot blocks, clamp blocks, and rods that are implanted along a patient's spine to fix two or more adjacent vertebrae relative to one another. The system generally includes a swing bolt anchor screw, a pivot block receivable on the swing bolt, and a clamp block receiving a rod therethrough that is pivotally attachable to the pivot block. In addition, the system includes one or more fixed anchor screws, and clamp assemblies for receiving the rod therein. The clamp assemblies and pivot block are receivable on the anchor screws by spindles that thread along a threaded portion of the anchor screws.

During use, vertebrae to be treated are surgically exposed, and an arrangement of anchor screws and clamp accessories are selected. For example, a fixed anchor screw may be screwed into each of the vertebrae on either side of a first vertebra. A rod is selected that may extend between the fixed anchor screws and that may be bent to conform to the shape of the anatomy encountered. The rod is inserted through a loose clamp block, and the rod is placed in clamp assemblies that are received over the fixed anchor screws.

A swing bolt anchor screw is then screwed into the first vertebra adjacent the rod, and a pivot block is received on the swing bolt screw. The clamp block and/or pivot block are adjusted such that the clamp block may be engaged with a pivot on the pivot block. A set screw may then be screwed into the clamp block to secure the clamp block to the pivot. A pair of set screws are also screwed into the clamp block to secure the rod within the clamp block. Preferably, a pair of such systems are implanted on either side of the vertebrae.

During the procedure, it may be desirable to adjust the vertebrae relative to one another. Once the system(s) is(are) connected as described above, the set screws may be loosened and the rod(s), clamp block(s), and/or pivot block(s) may be adjusted, e.g., by moving the spindle(s) to adjust the height of the pivot block(s) and/or clamp assemblies on the anchor screws, by pivoting the swing bolt anchor screw(s), and/or pivoting the clamp block(s) relative to the pivot block(s). Once the vertebrae have been moved into a desired position, the set screws may be tightened, and the spindles secured in position by crimping the walls surrounding the spindles.

An advantage of this system is that the swing bolt anchor screw, pivot block, and clamp block arrangement allows the system to be adjusted about two axes, i.e., the axis of the swing bolt anchor screw and the axis of the pivot on the pivot block. However, because the system of the '166 patent is polyaxial, i.e., may pivot about multiple axes, there is greater risk of the system coming out of alignment when the patient resumes normal physical activity.

This system is also very complicated, involving six parts, including three set screws, that are mounted on each swing bolt anchor screw. In addition, because the swing bolt is threaded, an intricate spindle device is required in order to allow the pivot block and clamp assemblies to be threaded onto the swing bolt, and still control their orientation about the axis of the swing bolt. Thus, because of its complexity and many intricate parts, this system may be expensive to manufacture and/or difficult to implant.

Accordingly, apparatus and methods for stabilizing, adjusting, and/or fixing vertebrae would be considered useful.

SUMMARY OF THE INVENTION

The present invention is directed to spinal fixation systems that may be secured between adjacent anchor screw assembles, e.g., to rods extending between the anchor screw assemblies, and to methods for stabilizing, adjusting, or otherwise fixing adjacent vertebrae using such spinal fixation systems.

In accordance with one aspect of the present invention, a spinal fixation system is provided that includes a first anchor screw assembly including a first passage and a first screw, the first screw having a threaded portion configured to be screwed into a first vertebra, and a second anchor screw assembly including a second passage and a second screw, the second screw having a threaded portion configured to be screwed into a second vertebra adjacent the first vertebra. In an exemplary embodiment, one or both of the anchor screw assemblies may include a saddle or clamp assembly receivable on the respective screw, each saddle assembly including a rod passage therethrough defining the first and second passages. Preferably, the saddle assemblies include upper and lower saddles or clamp portions that may together define the rod passage.

A rod or other elongate member is receivable in the first and second passages, the elongate member including an exposed portion extending between the first and second anchor screw assemblies. A spacer is securable on the exposed portion of the elongate member, the spacer having a length substantially similar to a length of the exposed portion of the elongate member for preventing the first and second anchor screw assemblies from moving towards one another.

In accordance with another aspect of the present invention, a kit is provided for stabilizing vertebrae relative to one another. Generally, the kit includes one or more substantially rigid rods, and a plurality of "C" shaped spacers having a plurality of lengths, the spacers including opposing edges defining a pocket therebetween for receiving the one or more rods therein. The kit may also include a plurality of anchor screw assemblies, the anchor screw assemblies including anchor screws and a plurality of clamp assemblies for receiving the one or more rods therein.

Optionally, the kit may also include a tool for crimping at least a portion of the opposing edges of the spacers around the one or more rods to secure the spacers to the rods. In another option, the kit may include an apparatus for bending the one or more rods, e.g., to conform substantially to a natural curvature of a patient's spinal column being treated.

In accordance with still another aspect of the present invention, a method is provided for stabilizing vertebrae relative to one another, the vertebrae being disposed adjacent one another along a central spinal axis. A first anchor screw may be screwed into a first vertebra, and a second anchor screw may be screwed into a second vertebra adjacent the first vertebra. A rod or other elongate member may be secured between the first and second anchor screws, e.g., using clamp assemblies, thereby fixing a relative distance of the first and second vertebrae.

A spacer, e.g., a "C" shaped clip, may be secured or otherwise placed on the elongate member, e.g., by crimping the spacer around the elongate member. Preferably, the spacer extends substantially an entire length of the elongate member that is exposed between the first and the second anchor screws to prevent the first and second anchor from moving towards one another. For example, the spacer may abut clamp assemblies on the first and second anchor screws, thereby preventing the clamp assemblies, and consequently the anchor screws, from moving substantially towards one another. One or both of the clamp assemblies may have a tapered side portion to enhance abutment of the spacer and the clamp assemblies if the elongate member is bent, e.g., to conform to the natural curvature of the anatomy encountered.

In accordance with yet another aspect of the present invention, an anchor screw assembly is provided that includes a screw having a first threaded portion, and a second head portion. A swing bolt is pivotally coupled to the second portion of the screw. The swing bolt defines a first axis, and includes a noncircular region extending along the first axis, the noncircular region having a noncircular cross-section and a substantially smooth wall. In addition, the swing bolt may include a threaded region on its end opposite the screw.

A clamp assembly may be provided that includes first and second clamp portions that are receivable on the swing bolt. Each clamp portion has a noncircular first passage therethrough for receiving the noncircular region of the swing bolt therethrough. Thus, the noncircular region and the first passage have like cross-sections, thereby preventing rotation of the clamp assembly with respect to the swing bolt about the first axis when the noncircular region of the swing bolt is received in the first passages.

In addition, the first and second clamp portions have cooperating grooves therein, the cooperating grooves together defining a second passage extending along a second axis substantially transversely to the first axis when the first and second clamp portions are received on the swing bolt.

A fastener, e.g., a nut, is also provided for securing the clamp assembly on the swing bolt, e.g., that may be threaded onto the threaded region of the swing bolt to secure the clamp assembly on the swing bolt. In a preferred embodiment, the second portion of the screw includes a shoulder, and the clamp assembly may substantially engage the shoulder when the clamp assembly is fully secured on the swing bolt, thereby preventing the swing bolt from pivoting with respect to the screw.

In accordance with still another aspect of the present invention, a spinal fixation system is provided that includes a first anchor screw assembly, such as that described above. The first anchor screw assembly includes a first screw having a threaded portion, and a swing bolt pivotally coupled to the screw and including a noncircular region. The spinal fixation system also includes a plurality of clamp assemblies, including a first passage for receiving the first swing bolt therethrough, and a second passage for receiving an elongate member, e.g., a substantially rigid rod, therethrough. The dimensions of each clamp assembly may be different, e.g., including a second passage that is at one of a plurality of distances from the first passage and/or that is oriented at a predetermined angle along the clamp assembly. A fastener may be used for securing a selected clamp assembly on the swing bolt. Thus, when the selected clamp assembly is received on the first swing bolt, the first clamp assembly is fixed in a predetermined orientation with respect to a first pivot axis of the first swing bolt.

The spinal fixation system also includes a second anchor screw assembly including a second screw having a threaded portion and a hub, and a second selected clamp assembly receivable on the hub. The second screw may be a fixed screw or, preferably, a swing bolt anchor screw, similar to that described above. The second clamp assembly includes a third passage therethrough along a third axis. The second screw assembly may be oriented, when implanted, such that the third axis is substantially transverse to the first axis. Optionally, additional anchor screw assemblies may also be provided.

In accordance with another aspect of the present invention, a method is provided for simple alignment or otherwise stabilizing vertebrae relative to one another using a plurality of swing bolt anchor screw assemblies, such as those described above. A threaded portion of a first swing bolt anchor screw is screwed into a first vertebra until a first pivot axis of the first swing bolt anchor screw is generally parallel to the spinal axis. A threaded portion of a second swing bolt anchor screw is screwed into a second vertebra adjacent the first vertebra until a second pivot axis of the second swing bolt anchor screw is substantially transverse to the first pivot axis. If desired, a third anchor screw (or more) may be screwed into other vertebra adjacent to the first vertebra.

An angle of one or more swing bolts on the first and second swing bolt anchor screws may be adjusted about the first and second pivot axes. Lower clamp portions may be placed on the swing bolts of the first and second swing bolt anchor screws, either before or after the angle adjustments described above. A rod may be placed on the lower clamp portions, e.g., when the grooves in the lower clamp portions have been properly aligned with one another. Thus, the rod may extend between the first and second anchor screws, and between any additional anchor screws added generally in a straight line. In addition, if desired, the rod may be bent, e.g., in a single plane, to a predetermined configuration based upon anatomy encountered before securing the rod on the swing bolts.

Upper clamp portions may be secured on the swing bolts of the first and second swing bolt anchor screws, thereby securing the rod between the upper and lower clamp portions. For example, a nut or other fastener may be threaded onto the swing bolt after the upper and lower clamp portions, thereby securing the rod between the upper and lower clamp portions and/or securing the clamp assemblies on the swing bolts. These fasteners may also be loosened to allow adjustment of the vertebrae relative to one another, and then the fasteners may again be tightened to fix the vertebrae in desired relative positions. Optionally, a spacer, such as that described above, may be secured between the clamp assemblies to prevent movement of the swing bolts towards one another.

Other objects and features of the present invention will become apparent from consideration of the following description taken in conjunction with the accompanying drawings.

BRIEF DESCRIPTION OF THE DRAWINGS

FIG. 3A is a perspective view of a preferred embodiment of an anchor screw assembly, in accordance with the present invention.

FIG. 3B is an exploded perspective view of the anchor screw assembly of FIG. 3A.

FIGS. 4A and 4B are perspective and side views, respectively, of a screw for the anchor screw assembly of FIGS. 3A and 3B.

FIGS. 5A–5C are perspective and first and second side views, respectively, of a swing bolt for the anchor screw assembly of FIGS. 3A and 3B.

FIGS. 6A–6C are perspective and first and second side views, respectively, of an assembled screw and swing bolt for the anchor screw assembly of FIGS. 3A and 3B.

FIGS. 7A–7C are perspective and first and second side views, respectively, of a first embodiment of a lower clamp portion for a clamp assembly, in accordance with the present invention.

FIGS. 8A–8C are perspective and first and second side views, respectively, of a first embodiment of an upper clamp portion for a clamp assembly, in accordance with the present invention.

FIG. 14 is a perspective view of another preferred embodiment of an anchor screw assembly, in accordance with the present invention.

FIGS. 15A and 15B are top and front views, respectively, of an upper clamp portion for use with the anchor screw assembly of FIG. 14.

FIG. 15C is a front view of an alternative embodiment of an upper clamp portion for use with the anchor screw assembly of FIG. 14.

DETAILED DESCRIPTION OF THE PREFERRED EMBODIMENTS

Figure 1A:
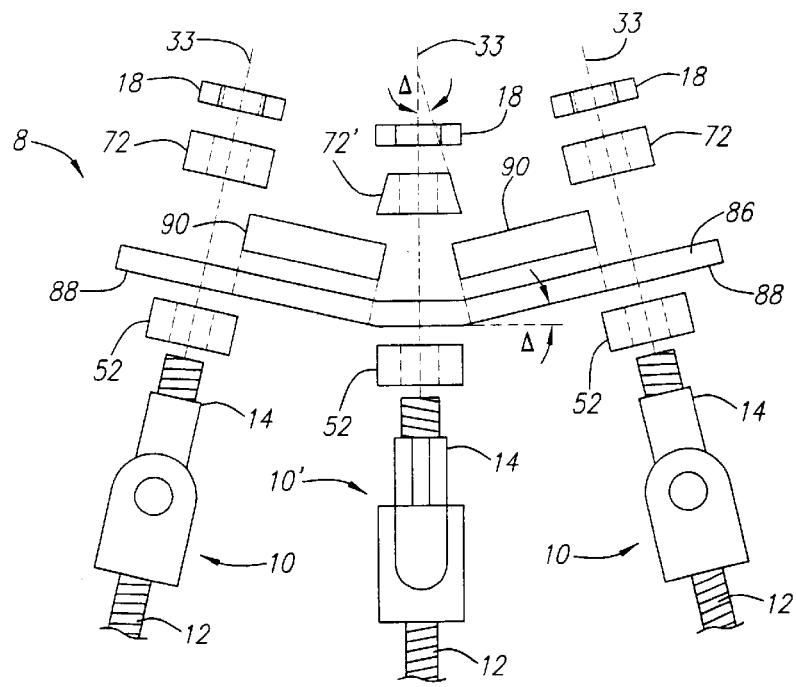
FIG. 1A is an exploded side view of a spinal fixation system, in accordance with the present invention.
Figure 1B:
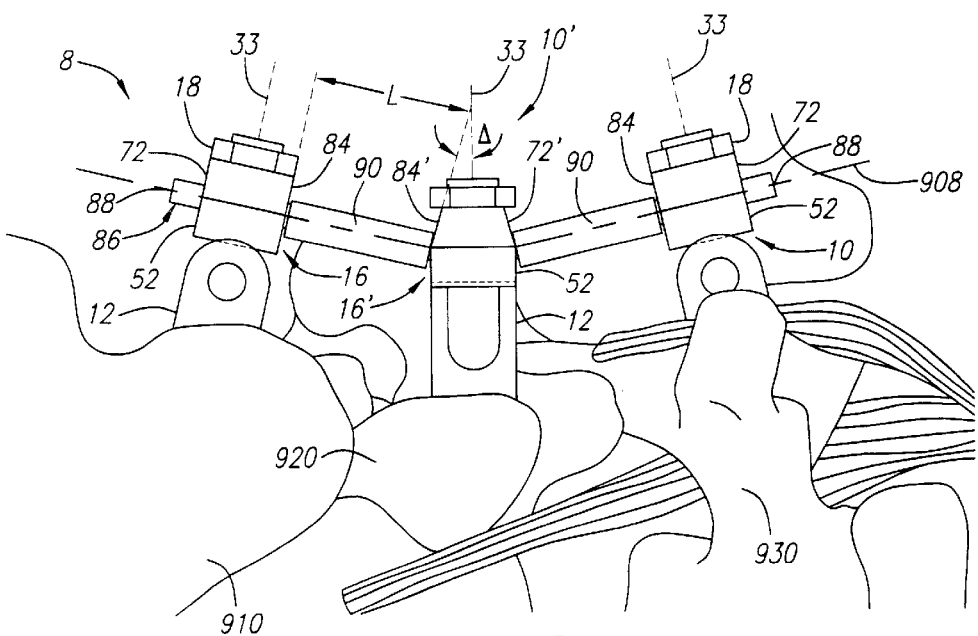
FIG. 1B is a side view of the system of FIG. 1A implanted to stabilize a plurality of vertebrae.

Turning now to the drawings, FIGS. 1A and 1B show a preferred embodiment of a spinal fixation system 8, in accordance with the present invention. Generally, the system 8 includes a plurality of anchor screw assemblies, 10, a rod 86 securable between the anchor screw assemblies 10, and one or more spacer clips 90 securable to the rod 86. All of the components of the system 8 may be made from a variety of biocompatible materials, e.g., metals, and preferably from titanium or alloys including titanium.

The rod 86 may be a substantially rigid elongate member, e.g., a solid rod, having a generally round cross-section. Optionally, the rod 86 has one or more flattened regions (not shown) extending between ends 88 of the rod 86. For example, the rod 86 may include opposing flattened regions (not shown), thereby defining a flattened elliptical cross-section. Optionally, the rod 86 may include serrations or teeth (not shown) extending between the ends 88, which may facilitate securing the rod 86 to the anchor screw assemblies 10.

The rod 86 may be substantially straight initially (not shown), and may be bent and/or curved during a procedure, e.g., to conform to the natural curvature or lordosis of the anatomy encountered, as shown in FIG. 1A, and as described further below. The rod 86 is sufficiently rigid, however, such that, once bent, the rod 86 may substantially retain its bent shape when subjected to forces experienced during normal activity of a patient, as will be appreciated by those skilled in the art.

Figure 2A:
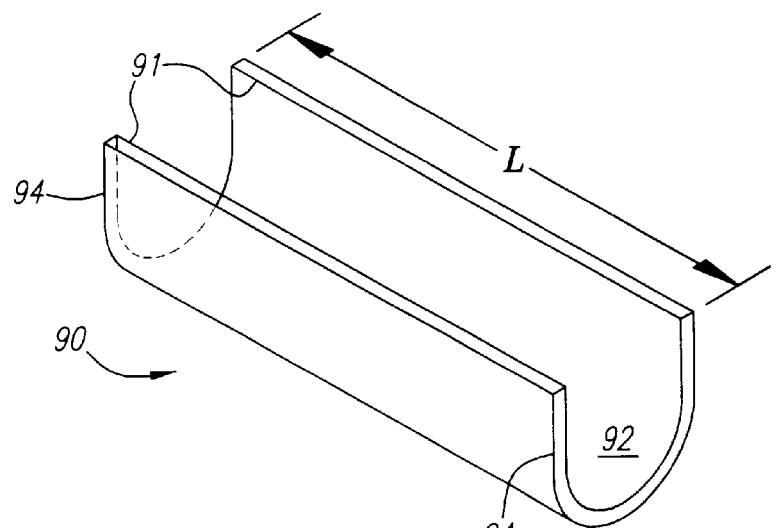
FIG. 2A is a perspective view of a spacer clip, in accordance with the present invention.
Figure 2B:
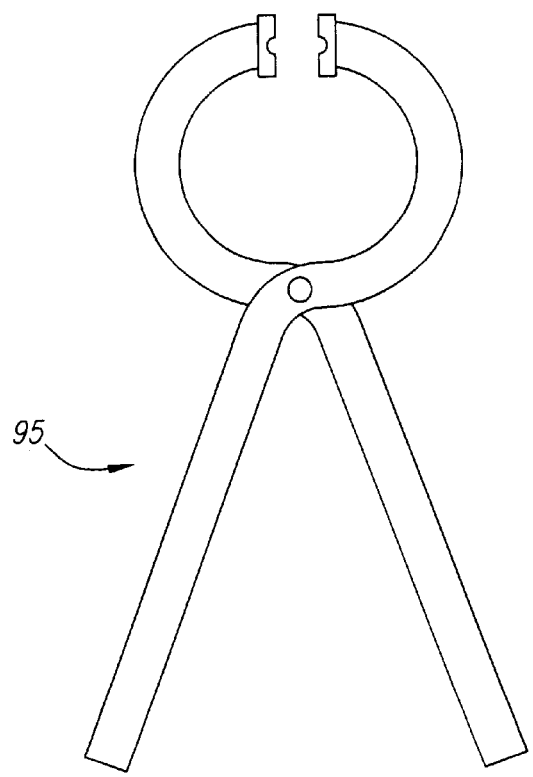
FIG. 2B is a side view of a crimping tool for use with the spacer clip of FIG. 2A.

Turning to FIG. 2A, a spacer clip 90 is shown that may be secured to the rod 86. Generally, the clip 90 is a "C" shaped member including opposing edges 91 defining a pocket 92 that extends between ends 94 of the clip 90. The pocket 92 has a cross-section that is larger than the rod 86 such that the clip 90 may be received at least partially around the rod 86. The clip 90 may be malleable such that a tool, such as the crimping tool 95 shown in FIG. 2B, may be used to crimp or otherwise compress at least portions of the opposing edges 91 around the rod 86 after the clip 90 has been placed on the rod 86 to secure the clip 90 to the rod 86.

A variety of clips may be provided, e.g., having standard lengths "L" and/or cross-sections. For example, a set of clips (not shown) may be provided that have lengths from about one to about three centimeters (1–3 cm), e.g., at 0.125 centimeter intervals. The ends 94 of the clip 90 are preferably substantially square, although alternatively, they may be tapered, e.g., such that the length of the clip as measured along the edges 91 is greater than the length as measured from the bottom of the pocket 92 (not shown).

Turning to FIGS. 3–8, each of the anchor screw assemblies 10 includes a screw 12, a swing bolt 14 pivotally coupled to the screw 12 to provide an anchor screw 15, and a clamp assembly 16 securably received on the swing bolt 14, as shown in FIGS. 3A and 3B. Alternatively, other anchor screw assemblies may be used to provide a system in accordance with the present invention. For example, a rigid anchor screw 90, such as that shown in FIGS. 11A and 11B, may be used instead of an anchor screw 15 including a swing bolt 14. In a further alternative, other anchor screw assemblies may be used, e.g., including saddle or clamp assemblies mounted on screw bolts, such as those disclosed in U.S. Pat. Nos. 4,653,481, 5,487,744, and 5,545,166, the disclosures of which are expressly incorporated herein by reference. Thus, any known anchor screw assemblies may be used, although the anchor screw assemblies shown and described herein may be particularly advantageous.

Turning to FIGS. 4A and 4B, the screw 12 of the anchor screw 15 generally includes a first threaded portion 20 terminating in a tip 22, and a second head portion 24 opposite the tip 22. The threaded portion 20 may include a helical thread 21 defining a thread pattern, preferably configured for substantially securing the screw 12 into bone, such as a portion of a vertebra (not shown). The thread spacing may be between about three to six threads per centimeter (3–6 threads/cm), and preferably about 4.8 threads per centimeter (about 12 threads per inch). The thread spacing may be substantially constant between the tip 22 and the head portion 24 or may vary along the length of the threaded portion 20.

The leading and trailing edges of axially adjacent portions of the thread 21 may define an inclusive angle "α" between them of between about twenty to forty degrees (20–40°), and preferably about thirty degrees (30°). Preferably, each thread 21 is rounded or tapers outwardly from the root diameter to the major diameter of the thread 21, such that the leading and trailing edges on either side of a portion of the thread 21 define tangent lines that intersect one another adjacent the outer edge of the respective portion of the thread 21. The thread 21 may have a height of between about 0.50–3.00 millimeters, and preferably between about 0.60–2.00 millimeters.

The threaded portion 20 may have desired dimensions to accommodate threading into bone, such as a vertebra (not shown). For example, the threaded portion 20 may have an outer diameter between about 3.5–8.5 millimeters, preferably between about 5.8–8.5 millimeters, and a length between about 25–65 millimeters, and preferably between about 35–65 millimeters. The threaded portion 20 may have a substantially uniform major and minor diameter along its length. Alternatively, the threaded portion 20 may have a taper, e.g., reducing in minor and/or major diameter from the head portion 24 towards the tip 22. The thread 21 may have a substantially uniform height, or may become increasingly higher from the head portion 24 towards the tip 22, e.g., if the threaded portion 20 is tapered, to provide a substantially uniform outer diameter for the threaded portion 20.

In addition, the threaded portion 20 may include a pull-out portion 21A, which may facilitate manufacturing of the anchor screw 12 and/or may improve engagement of the screw 12 with bone into which the screw 12 is threaded. Other thread patterns and screw designs may also be used for an anchor screw assembly in accordance with the present invention, as found in U.S. Pat. Nos. 4,854,311, 5,034,011, and 5,226,766, the disclosures of which are expressly incorporated herein by reference.

The head portion 24 generally has a cross-section larger than the threaded portion 20 and includes a full-radius shoulder 28 opposite the threaded portion 20. The shoulder 28 includes a predetermined radius about a pivot axis 35 to facilitate pivoting of the swing bolt 14 and/or the clamp assembly 16 (shown in FIGS. 3A and 3B) with respect to the head portion 24, as explained further below. The head portion 24 includes a slot 30 therein extending generally parallel to a longitudinal axis 32 of the screw 12, thereby dividing the head portion 24 into ears 26. Pin holes 34 extend through the ears 26 along the pivot axis 35, i.e., substantially perpendicular to the longitudinal axis 32.

Turning to FIGS. 5A–5C, the swing bolt 14 includes an elongate body 34 including a first looped region 36, a second noncircular intermediate region 38, and a third threaded region 40 generally opposite the looped region 36. The looped region 36 may be substantially narrower than the other regions of the swing bolt 14, i.e., having a width slightly smaller than a width of the slot 30 in the screw 12 such that the looped region 36 may be received in the slot 30 between the ears 26, as shown in FIGS. 6A–6C. The looped region 36 has a pin hole 37 therethrough that extends substantially perpendicular to the longitudinal axis 32.

The noncircular region 38 of the swing bolt 14 is preferably substantially smooth-walled and has a noncircular cross-section, preferably for slidably receiving the clamp assembly 16 thereon (as shown in FIGS. 3A and 3B), while preventing rotation of the clamp assembly 16 about longitudinal axis 33. In the preferred embodiment shown in FIGS. 5A–5C, one or more flat walls 42, and preferably two opposing flat walls, are formed along the intermediate region 38. Thus, the cross-section may define a flattened elliptical shape, a "D" shape. Alternatively, other shapes may be used, such as a hexagon, a square, a star, or other noncircular geometric shape.

As shown in FIGS. 6A–6C, the looped region 36 of the swing bolt 14 may be received in the slot 30 of the head portion 24, and a pin 44 may be received through the pin holes 34, 37 to provide anchor screw 15. The pin 44 may fix the swing bolt 14 to the screw 12, while allowing the swing bolt 14 and screw 12 to pivot with respect to one another such that the longitudinal axes 32, 33 intersect, but define an angle "theta" greater than zero degrees, as shown in phantom in FIG. 6B.

Turning to FIGS. 7A–8C, the clamp assembly 16 (shown in FIGS. 3A and 3B) generally includes a first lower clamp portion 52 and a second upper clamp portion 72. The lower and upper clamp portions 52, 72 have noncircular bolt passages 54, 74 that extend entirely through them between lower surfaces 56, 76 and upper surfaces 58, 78, respectively, thereby defining a first axis 60. The bolt passages 54, 74 preferably have a cross-section similar to the cross-section of the noncircular region 42 of the swing bolt 14 (see FIGS. 3B, 5A, 5B, 6A, and 6B). Thus, the bolt passages 54, 74 may accommodate receiving the swing bolt 14 therethrough, while preventing rotation of the clamp assembly 16 on the swing bolt 14, as explained further below.

In addition, the lower and upper clamp portions 52, 72 have generally semi-cylindrical grooves 62, 82 therein that cooperate with one another when the clamp assembly 16 is assembled to define a rod passage 64, as shown in FIG. 3A. The rod passage 64 generally extends along a second axis 66 that is transverse to, and preferably substantially perpendicular to, the first axis 60. In the embodiment shown, the second axis 66 is also substantially perpendicular to a third axis 70 that extends along a length of the lower clamp portion 52 substantially perpendicular to both the first and second axes 60, 66 (thus, the three axes 60, 66, 70 may be orthogonal to one another). The rod passage 64 has a cross-section similar to a rod 86 (not shown, see FIG. 1A) that may be received therein. For example, the cross-section may be generally circular, but optionally may be noncircular, e.g., circular with one or more flattened walls, such as wall 83 shown in the upper clamp portion 72 in FIGS. 8B and 8C. Alternatively, as shown in FIG. 3A, the rod passage 64 may have other geometric shapes, similar to the bolt passages 54, 74, described above. In a further alternative, one or both of the grooves 62, 82 may include teeth or other serrations (not shown) for enhancing engagement with the rod received in the rod passage 64 (shown in FIG. 3A), either alone or in combination with one of the cross-sections described above. Exemplary serrations are shown in U.S. Pat. Nos. 4,653,481 and 5,545,164, the disclosures of which are expressly incorporated herein by reference.

With particular reference to FIGS. 8A–8C, the groove 82 in the upper clamp portion 72 extends along the lower surface 76. The upper surface 78 may be recessed around the bolt passage 74, thereby accommodating a fastener (not shown) thereon, while minimizing the profile of the resulting clamp assembly. For example, the groove 82 may define a hump 79 opposite the lower surface 76, which may be higher than the upper surface 78. The hump 79 may have a height similar to a nut or other fastener (not shown) that may be attached to a swing bolt (also not shown) that is inserted through the bolt passage 74. Thus, when a fastener 18 (not shown, see FIG. 3A) engages the upper surface 78, the upper surface of the fastener 18 may define a height similar to the hump 79 (also as shown in FIG. 3A), thereby substantially minimizing a profile of the anchor screw assembly and/or reducing tissue irritation.

Returning to FIGS. 8A–8C, side edges 84 of the upper clamp portion may be substantially square with the lower surface 76, i.e., the side edges 84 may extend substantially parallel to the first axis 60. Alternatively, as shown in FIGS. 15A and 15B, the side edges 84' may be tapered. For example, the side edges 84' of the upper clamp portion 72' may taper inwardly towards the hump 79' such that they define an angle Δ between about one and twenty degrees (1–20°) with the first axis 60', and preferably about ten degrees (10°). Such a taper may be machined into the side edges 84' or formed using other known methods.

Alternatively, as shown in FIG. 15C, instead of tapering the side edges 84, the side edges 84 may be substantially square, and a spot face, recess, or notch 85" may be formed around the groove 82," e.g., by spot facing the side edges 84." These tapered or recessed features may enhance abutment with ends 94 of the spacer clip 90 despite the natural curvature or lordosis of a spinal column (not shown) when the spacer clip 90 is secured to a curved rod 86 (not shown, see FIGS. 1A and 1B), as explained further below.

Turning to FIGS. 7A–7C, the groove 62 in the lower clamp portion 52 extends along the upper surface 58. In addition, the lower clamp portion 62 also includes a recess 68 in the lower surface 56 that intersects the bolt passage 54. The recess 68 preferably has a radius of curvature similar to the shoulder 28 on the head portion 24 of the screw 12 (see FIGS. 6A–6C), as explained further below.

Returning to FIGS. 3A, 3B, 7C, and 8C, the lower surface 76 of the upper clamp portion 72 and the upper surface 58 of the lower clamp portion 52 are substantially flat such that the lower and upper clamp portions 52, 72 may substantially abut one another to provide the rod passage 64. Alternatively, the upper and lower surfaces 58, 76 may include mating segments, e.g., cooperating tabs and slots or other male/female connectors (not shown), that may positively engage one another when the lower and upper clamp portions 52, 72 are disposed in the proper orientation.

The clamp assembly 16 may be received on the swing bolt 14, e.g., by orienting the clamp assembly 16 such that the bolt passages 54, 74 are properly aligned with the noncircular region of the swing bolt 14. The lower clamp portion 52 may be directed over the swing bolt 14 and then the upper clamp portion 72 may be received over the swing bolt 14, i.e., through the bolt passages 54, 74, respectively. A fastener, e.g., nut 18, may be threaded onto the threaded region 40 of the swing bolt 14 until it engages upper surface 78 of the upper clamp portion 72, thereby forcing the clamp assembly 16 towards the head portion 24 of the screw 12. Consequently, the lower clamp portion 52 may abut the head portion 24 such that the shoulder 28 is received in the recess 68 in the lower surface 56.

Preferably, because of the mating shapes of the shoulder 28 and recess 68, the lower clamp portion 52 may slide along the shoulder 28 as the swing bolt 14 is pivoted with respect to the screw 12. Once a desired angle is obtained, the nut 18 may be further tightened until the wall of the recess 68 frictionally engages the shoulder 28, thereby substantially securing the swing bolt 14 at the desired angle relative to the screw 12.

Figure 9A:
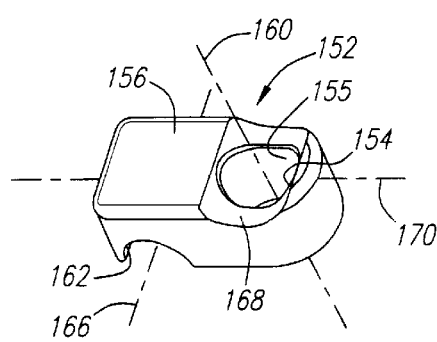
FIGS. 9A–9E are perspective views of alternative embodiments of a lower clamp portion, in accordance with the present invention.

Turning to FIGS. 9A–10E, several alternative embodiments of lower and upper clamp portions are shown that together may provide clamp assemblies that may be received over the screw assembly 15 of FIGS. 6A–6C. For example, the lower and upper clamp portions 152, 172 shown in FIGS. 9A and 10A are generally similar to that shown in FIGS. 7A and 8A, except that the flat regions 155, 175 of the bolt passages 154, 174 and the recess 168 are offset ninety degrees from the previous embodiment. The resulting clamp assembly (not shown) may be mounted similar to the previous embodiment, but offset ninety degrees with respect to the anchor screw (not shown).

Figure 9B:
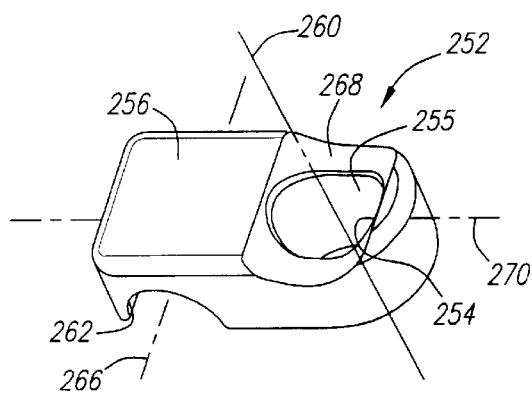
Figure 10A:
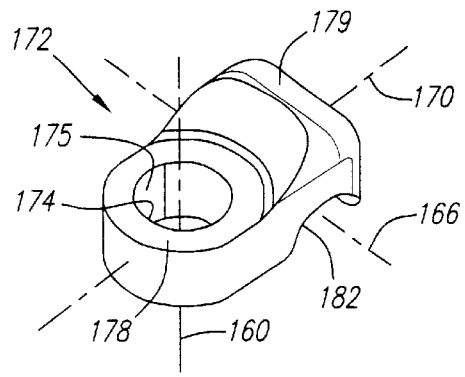
FIGS. 10A–10E are perspective views of alternative embodiments of an upper clamp portion, in accordance with the present invention.
Figure 10B:
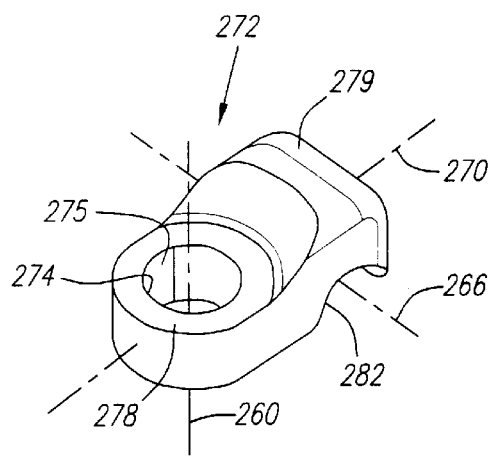

Turning to FIGS. 9B and 10B, another set of lower and upper clamp portions 252, 272 are shown that are similar to the embodiments of FIGS. 9A and 10A, except that the grooves 262, 282 are located further away from the bolt passages 254, 274 along the third axis 270. The resulting clamp assembly from these embodiments may be mounted on the anchor screw similar to the previous embodiment with the shoulder 28 of the screw 12 being received in the recess 268. A rod (not shown) received in the resulting rod passage, however, will be disposed further from the anchor screw than the previous embodiment.

Figure 9C:
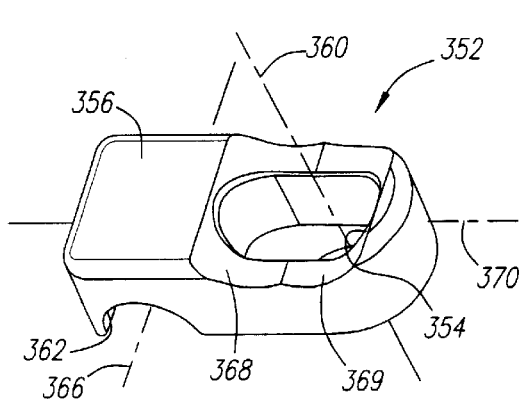
Figure 10C:
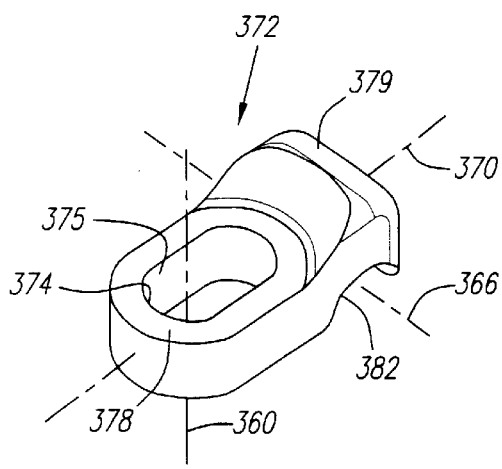

Turning to FIGS. 9C and 10C, yet another set of lower and upper clamp portions 352, 372 are shown that are similar to the embodiments of FIGS. 9A and 10A, except that the bolt passages 354, 374 have an elongated elliptical shape extending along the third axis 370. In addition, the lower surface 356 of the lower clamp portion 352 includes adjacent recesses 368, 369 that intersect the bolt passage 354 and may overlap one another. The resulting clamp assembly from this embodiment may be secured to the anchor screw such that either of the recesses 368, 369 slidably engages the shoulder of the screw (not shown), thereby allowing a rod (also not shown) received in the rod passage to be disposed at two possible locations, e.g., distances, relative to the anchor screw. Optionally, more than two recesses (not shown) may be provided, thereby allowing the rod passage to be disposed at multiple distances from the anchor screw.

Figure 9D:
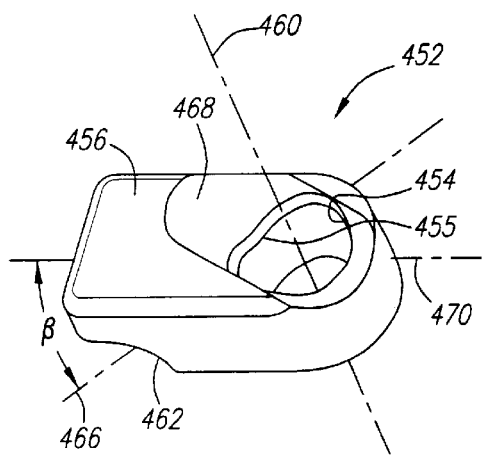
Figure 10D:
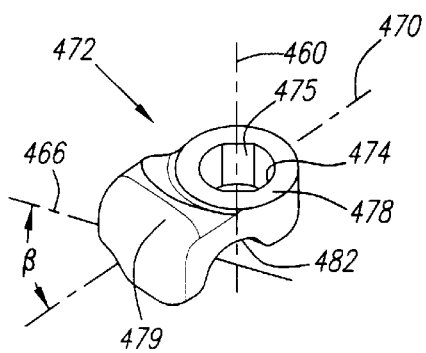

Turning to FIGS. 9D and 10D, still another set of lower and upper clamp portions 452, 472 are shown that are similar to the embodiments of FIGS. 7A and 8A, except that the grooves 462, 482 and recess 468 are aligned such that the second axis 466 defines an angle "β" with the third axis 470. Preferably, the angle "β" is between about ten and seventy degrees (10–75°), and more preferably between about thirty and forty five degrees (30–45°). In addition, the flattened wall regions 455, 475 are aligned substantially parallel to the second axis 466, thereby also defining an angle "β" with respect to the third axis 470.

Figure 9E:
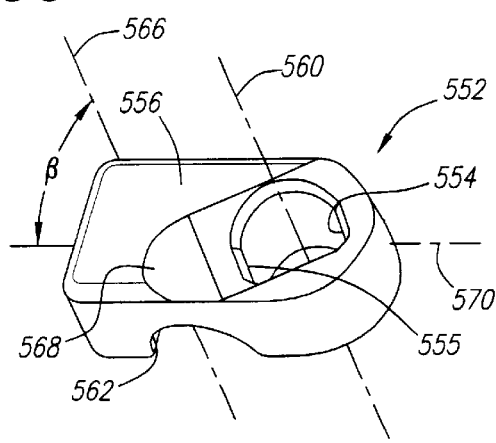
Figure 10E:
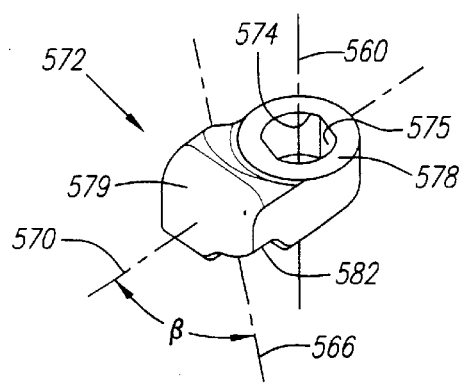

Turning to FIGS. 9E and 10E, another set of lower and upper clamp portions 552, 572 are shown that are similar to the embodiments of FIGS. 9D and 10D, except that the bolt passages 554, 574, recess 568, and grooves 562, 582 are mirror opposites or opposite-hand of those in the previous embodiment. Thus, it will be appreciated by those skilled in the art that a variety of clamp assemblies may be providing including a range of dimensions, e.g., lengths, thicknesses, "β" angles, and the like, in any combination or subcombination of the features described above.

Figure 11A:
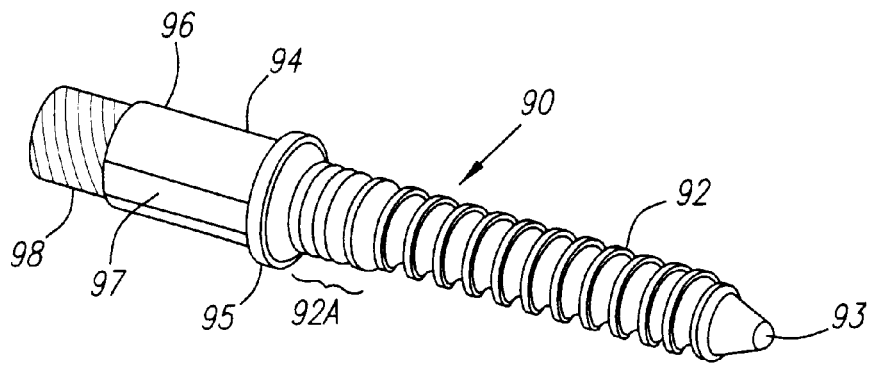
FIGS. 11A and 11B are perspective and side views, respectively, of another embodiment of an anchor screw, in accordance with the present invention.
Figure 11B:
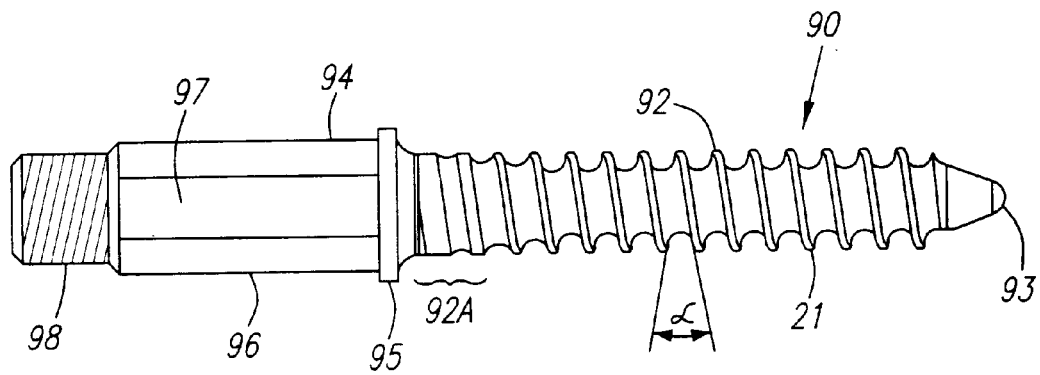

Turning to FIGS. 11A and 11B, another preferred embodiment of an anchor screw 90 is shown that includes a threaded portion 92 terminating in a tip 93, and an enlarged head portion 94 including a noncircular region 96 and a threaded region 98 opposite the tip 93. The threaded portion 92 may include any of the features and/or dimensions described above for the anchor screw 12 of FIGS. 4A–4C, e.g., thread pattern, outer diameter, taper, and the like. The threaded region 98 may receive a fastener, such as the nut described above (not shown), e.g., to substantially secure a clamp assembly (also not shown) on the noncircular region 96, similar to the embodiment described above. Thus, the anchor screw 90 may receive any of the clamp assemblies described above.

To select a system 8, such as that shown in FIGS. 1A and 1B, a kit may be provided (not shown). The kit may include a plurality of anchor screws, clamp assemblies, and fasteners that may be selected based upon the specific vertebrae being treated and/or based upon the anatomy encountered. Each anchor screw assembly may include an anchor screw, e.g., a pivoting or fixed anchor screw, and one or more clamp assemblies. For example, a plurality of upper and lower clamp assemblies may be provided, having different dimensions, as described above. An appropriate pair, corresponding to the patient anatomy encountered, may be selected for each anchor screw.

One or more rods may be provided, and an apparatus (not shown) may be provided for bending the rod(s) in a desired configuration during a procedure. Finally, a plurality of spacer clips may be provided, e.g., having different lengths, as described above, and a tool, e.g., a crimper or plyers, may be provided for crimping the spacer clip. Thus, a system in accordance with the present invention provides a modularity that may easily accommodate a variety of anatomy and patients.

Turning to FIGS. 12A–12C and 13, an exemplary system 1000 is shown that includes a pair of rods 1002 that are each implanted along a spinal column using three swing bolt anchor screws 1010–1014 and three clamp assemblies, 1016–1020. Alternatively, one or more of the swing bolt anchor screws, such as the outside anchor screws 1010, 1014, may be replaced with nonpivoting anchor screws (such as that shown in FIGS. 11A and 11B). In a further alternative, fewer or additional anchor screws may be implanted, e.g., to secure a shorter or longer rod and/or to fix fewer or additional vertebrae.

Figure 13:
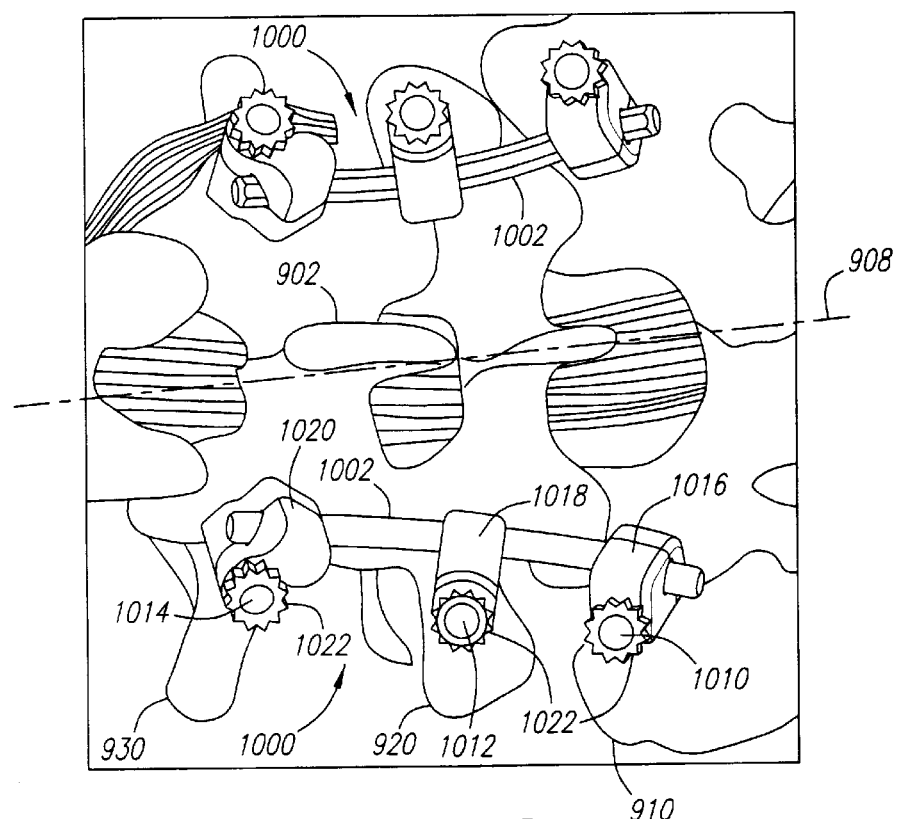
FIG. 13 shows a pair of spinal fixation systems implanted along a patient's spine, in accordance with the present invention.

Preferably, the rods 1002 are implanted generally parallel to the central spinal axis on either side of the spinous processes 902, as shown in FIG. 13. The system 1000 may be used to provide adjustment of the vertebrae, e.g., to allow vertical or horizontal, medial or lateral adjustment. Although an implantation procedure for only one rod 1002 is described below, it will be appreciated that a second rod (or even additional rods) may be implanted using a similar procedure.

Figure 12A:
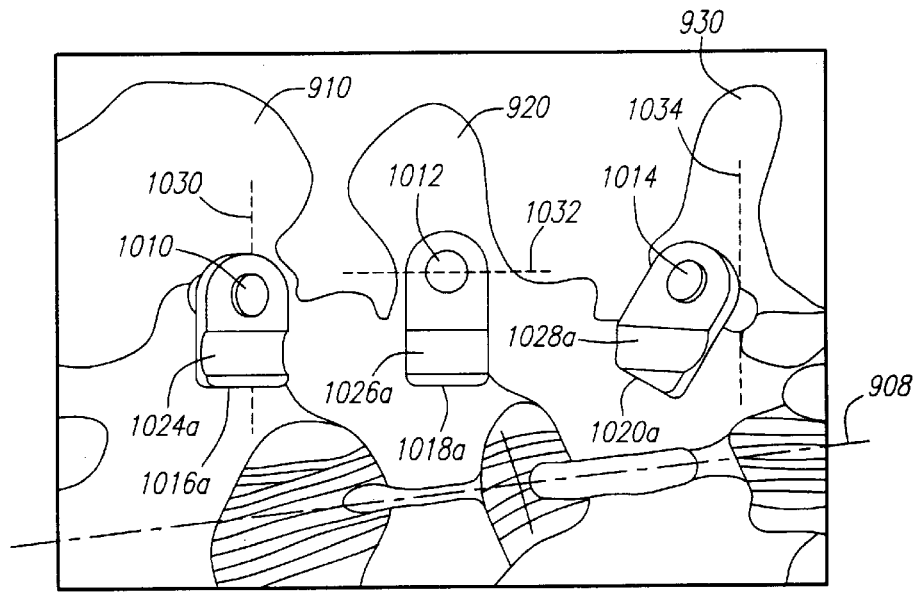
FIGS. 12A–12C show a spinal fixation system being implanted between vertebrae of a patient, in accordance with the present invention.

Turning first to FIG. 12A, the vertebrae, e.g., vertebrae 910, 920, 930, to be stabilized are exposed, e.g., using conventional surgical procedures. The anchor screws 1010–1014 are screwed into the vertebrae 910–930, respectively, e.g., into the pedicles. Preferably, the anchor screws 1010–1014 are screwed in sufficiently to provide a predetermined pivot axis with respect to a centerline spinal axis of the patient. For example, the anchor screw 1012 may be screwed into the pedicle until a pivot axis 1032 of the anchor screw 1012 is disposed generally parallel to the centerline spinal axis 908. In contrast, the other anchor screws 1010, 1014 may be screwed into their respective vertebrae until their respective pivot axes 1030, 1034 are disposed substantially transverse to the first pivot axis 1032, and preferably substantially perpendicular to the centerline spinal axis.

Clamp assemblies 1016–1020 are selected based upon the anatomy encountered. For example, the clamp assembly 1016 may be similar to the clamp assembly 52, 72 shown in FIGS. 7A and 8A, and the clamp assembly 1018 may be similar to the clamp assembly 152, 172 of FIGS. 9A and 10A, i.e., having a longer length than the clamp assembly 1016. Finally, the clamp assembly 1020 may be similar to the clamp assembly 452, 472 shown in FIGS. 9B and 10B, i.e., having a groove 1028a (see FIG. 12A) that extends in line with the grooves 1024a, 1026a of the clamp assemblies 1016, 1018.

The lower clamp portions 1016a–1020a of the clamp assemblies 1016–1020 may be received over the noncircular regions (not shown) of the anchor screws 1010–1014, as best seen in FIG. 12A.

Figure 12B:
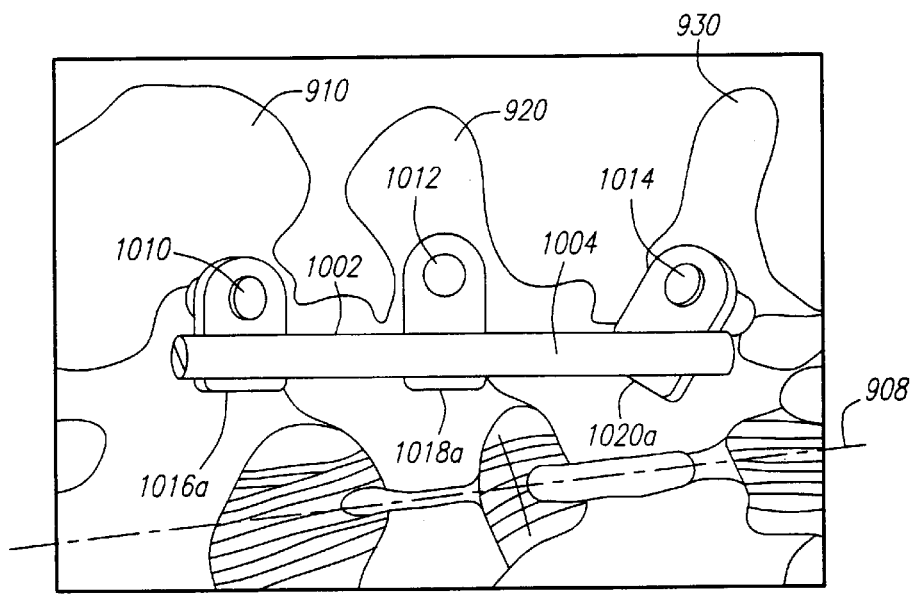

A rod 1002 may be received in the grooves 1024a–1028a in the lower clamp portions 1016a–1020a, thereby extending between the anchor screws 1010–1014, as shown in FIG. 12B. If desired, the rod 1002 may be bent to a predetermined shape, as needed, to conform to the anatomy alignment encountered. Preferably, the rod 1002 is bent in only one plane, e.g., the sagetal plane, while remaining substantially straight in the coronal plane, as shown in FIG. 1A. "Sagetal" plane, as used herein, refers to the plane that may be seen from a lateral view of the patient, e.g., that is viewed horizontally when the patient is lying face-down (such as the plane seen in FIGS. 1A and 1B). "Coronal" plane refers to the plane that may be seen from an anterior or posterior view of the patient, e.g., that is viewed vertically up the length of the spine when the patient is lying face-down (such as that shown in FIGS. 12A–12C).

Optionally, if the rod 1002 includes one or more flattened regions 1004, the flattened region(s) 1004 may be oriented so that they may engage similar flattened regions (not shown) in the rod passages 1024–1028 in the clamp assemblies 1016–1020 (e.g., in the upper clamp portions 1016b–1020b).

One or more of the clamp assemblies 1016–1020 may be adjusted at any time during the procedure. By adjusting the clamp assemblies 1016–1020, the swing bolts on the anchor screws 1010–1014 may be pivoted about their respective pivot axes 1030–1034 with respect to the threaded portions that have been threaded into the vertebrae 910–930. For example, the lower clamp portions 1016a–1020a may be adjusted before and/or after the rod 1002 is received in the grooves 1024a–1028a. Because the pivot axes 1030–1034 of the swing bolt anchor screws 1010–1014 are substantially transverse with respect to one another, a uniaxial device (i.e., pivoting in a single axis) may be used to provide multiple degrees of freedom for moving the clamp assemblies 1016–1020 relative to the rod 1002. This may minimize the amount of bending required of the rod 1002, preferably requiring bending in only one plane (preferably, the sagetal plane), thereby substantially maximizing the rigidity of the rod 1002.

Figure 12C:
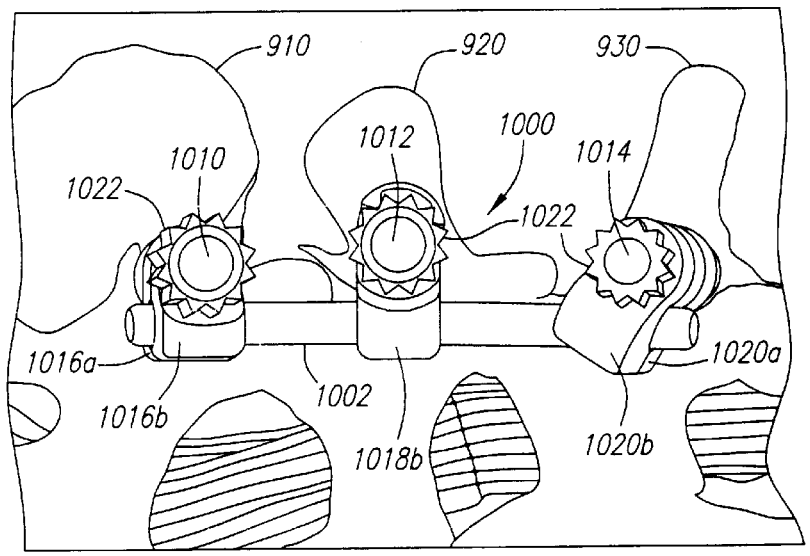

As shown in FIG. 12C, upper clamp portions 1016b–1020b may be placed on the lower clamp portions 1016a–1020a, i.e., received on the swing bolts of the anchor screws 1010–1014. When properly placed, the grooves (not shown) in the upper clamp portions 1016b–1020b substantially engage the rod 1002. Fasteners, such as nuts 1022, may then by threaded onto the swing bolts, thereby substantially securing the rod 1002 between the upper and lower clamp portions 1016–1020.

Preferably, the nuts 1022 are twelve point jam nuts. The nuts 1022 may have rounded upper edges, which may minimize tissue irritation, e.g., of tissue overlying the nuts 1022 after implantation of the system 1000. In addition, the nuts 1022 may include a crimpable rim (not shown), which may be crimped when the nuts are tightened to a desired torque, e.g., to prevent subsequent loosening of the nuts. Alternatively, hex nuts or other fasteners may be used.

Preferably, the lower clamp portions 1016a–1020a include radiused recesses (not shown) on their lower surfaces that intersect bolt passages for receiving the swing bolts 1010–1014 therein. These recesses may slidably engage similarly radiused shoulders on screws of the swing bolts (not shown), as described above. Thus, as the angles of the swing bolts are adjusted, the shoulders may pivotally slide along the surfaces of the recesses of the lower clamp portions 1016a–1020a. Once a desired configuration is obtained, the nuts 1022 may be tightened, thereby causing the lower clamp portions 1016a–1020a to frictionally engage the shoulders and secure the swing bolts with respect to the threaded portions without substantially moving one or more of the vertebrae out of the desired position.

If it is desired to adjust the vertebrae 910–930 with respect to one another, the nuts 1022 may be loosened, and the vertebrae 910–930 adjusted, thereby possibly changing the angle of one or more of the clamp assemblies 1016–1020 holding the rod 1002. Once a desired arrangement is obtained, the nuts 1022 may be tightened, thereby securing the clamp assemblies 1016–1020. Thus, with a system in accordance with the present invention, each individual clamp assembly is uniaxial, i.e., may only be pivoted about a single axis. By setting the axes of the anchor screws substantially transverse relative to one another, substantially flexibility may be obtained without substantially compromising vertebra position. Because of the uniaxial nature of the clamp assemblies, the system may be less likely to become misaligned when the patient resumes normal activity than a polyaxial system.

Once the final configuration of the clamp assemblies 1016–1020 and/or anchor screws 1010–1014 is determined, spacer clips 90 (not shown, see FIGS. 1A and 1B) may be placed on the rod 1004 between adjacent anchor screw assemblies.

For example, turning to FIGS. 1A and 1B, an exemplary system 8 is shown that has been implanted into vertebrae 910, 920, 930. After vertebral distraction or compression and before final tightening of the nuts 18, spacer clips 90 may be placed around and crimped to exposed portions of rod 86 that extends between adjacent clamp assemblies 10, 10'.

In this exemplary system 8, two anchor screw assemblies 10 including upper clamp portions 16 with square side edges 84 (such as that shown in FIG. 3A) and one anchor screw assembly 10' (such as that shown in FIG. 14) with an upper clamp portion 16' with tapered side edges 84' have been selected. Because of the natural curvature or lordosis defined by the vertebrae 910, 920, 930, the longitudinal axes 33 of adjacent anchor screws 15 may define an angle Δ relative to one another. To match this natural curvature, the rod 86 may be bent to also define an angle Δ.

The upper clamp portion 16' may be tapered, as described above with reference to FIGS. 15A and 15B, also to define an angle Δ relative to the longitudinal axis 33. With this anchor assembly 10' selected, the opposing side edges 84, 84' of the adjacent upper clamp portions 72, 72' may be oriented substantially parallel to one another, as best seen in FIG. 1B. The distance "L" between the opposing side edges 84, 84' may be measured, and an appropriate spacer clip 90, e.g., having a length approximately "L" (or less than "L"), i.e., corresponding substantially to the measured distance, may be placed on the exposed portion of the rod 86 between the adjacent clamp assemblies 16, 16'.

The spacer clip 90 may be crimped around the rod 86, e.g., by compressing the opposing edges 91 (not shown, see FIG. 2A) of the clip 90 using a crimper tool 95 (not shown, see FIG. 2B) to malleably deform the opposing edges 91 towards one another. The crimper tool 95 may be sufficiently long that a substantial length of the clip 90 may be engaged therein. Alternatively, one or more successive portions along the length of the clip 90 may be crimped around the rod 86 with the tool 95. This placement and crimping process may be repeated for each exposed portion of the rod(s) 90 extending between adjacent clamp assemblies 16, 16'.

The spacer clips 90 provide axial support, e.g., once the patient returns to a vertical position, thereby preventing the adjacent clamp assemblies 16, 16' from moving substantially towards one another. Thus, the spacer clips 90 may enhance the system 8 remaining in the final configuration set during the procedure and minimize any slippage of the system 8 once the patient resumes normal activity.

In a further alternative, if the sides of the upper clamp portions are not tapered, e.g., if the upper clamp portions include spotfaced angular recesses around the rod grooves (not shown), the ends of the clip(s) may be received in the recesses, thereby preventing the clip(s) from being dislocated from the rod once the patient assumes normal activity. For example, the patient may be placed under traction or the vertebrae may otherwise be distracted away from one another. This may provide sufficient space between the adjacent clamp assemblies to allow the spacer clip(s) to be placed around and/or otherwise secured to the rod(s). When distraction is removed, the vertebrae may return to a desired state, whereupon the spacer clip(s) substantially abut the adjacent clamp assemblies, thereby preventing axial movement of the clamp assemblies towards one another. In addition, the ends of the clip(s) may be received in the recesses in the sides of the clamp assemblies, thereby further securing the clip(s) relative to the rod. In still a further alternative, the spacer clips themselves may be tapered (not shown) to extend between and abut adjacent clamp assemblies.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

I claim:

1. A spinal fixation system, comprising:
   a first anchor screw assembly comprising a first passage and a first screw, the first screw having a threaded portion configured to be screwed into a first vertebra;
   a second anchor screw assembly comprising a second passage and a second screw, the second screw having a threaded portion configured to be screwed into a second vertebra adjacent the first vertebra;
   an elongate member receivable in the first and second passages for stabilizing the first and second vertebra with respect to each other, the elongate member comprising an exposed portion extending between the first and second anchor screw assemblies; and a "C" shaped spacer securable to the exposed portion of the elongate member by compressing the spacer onto the elongate member, the spacer having a length substantially similar to a length of the exposed portion of the elongate member for preventing the first and second anchor screw assemblies from moving substantially towards one another.

2. A spinal fixation system, comprising:
a first anchor screw assembly comprising a first passage and a first screw, the first screw having a threaded portion configured to be screwed into a first vertebra, wherein the first anchor screw assembly comprises a first clamp assembly receivable on the first screw assembly, the first clamp assembly comprising the first passage therethrough;
a second anchor screw assembly comprising a second passage and a second screw, the second screw having a threaded portion configured to be screwed into a second vertebra adjacent the first vertebra;
an elongate member receivable in the first and second passages for stabilizing the first and second vertebra with respect to each other, the elongate member comprising an exposed portion extending between the first and second anchor screw assemblies; and
a spacer securable to the exposed portion of the elongate member, the spacer having a length substantially similar to a length of the exposed portion of the elongate member for preventing the first and second anchor screw assemblies from moving substantially towards one another.

3. The spinal fixation system of claim 2, wherein the first clamp assembly comprises upper and lower clamp portions defining the first passage therebetween.

4. The spinal fixation system of claim 2, wherein the elongate member is at least partially curved, and wherein the first clamp assembly comprises a tapered side edge defining an angle corresponding to an angle of curvature defined by the elongate member.

5. A spinal fixation system, comprising:
a first anchor screw assembly comprising a first passage and a first screw, the first screw having a threaded portion configured to be screwed into a first vertebra, wherein the first screw comprises a head portion opposite the threaded portion comprising a shoulder, and wherein the first anchor screw assembly further comprises a swing bolt pivotally coupled to a second portion of the screw and a clamp assembly on the swing bolt comprising the first passage therethrough
a second anchor screw assembly comprising a second passage and a second screw, the second screw having a threaded portion configured to be screwed into a second vertebra adjacent the first vertebra;
an elongate member receivable in the first and second passages for stabilizing the first and second vertebra with respect to each other, the elongate member comprising an exposed portion extending between the first and second anchor screw assemblies; and
a spacer securable to the exposed portion of the elongate member, the spacer having a length substantially similar to a length of the exposed portion of the elongate member for preventing the first and second anchor screw assemblies from moving substantially towards one another.

6. The spinal fixation system of claim 5, wherein the swing bolt comprises a noncircular region, and wherein the clamp assembly comprises a passage having a noncircular cross-section similar to the noncircular region for seating the clamp assembly on the swing bolt.

7. The spinal fixation system of claim 6, wherein the swing bolt comprises a threaded region opposite the first screw, and wherein a fastener is threadable onto the threaded region for securing the clamp assembly on the swing bolt.

8. A spinal fixation system, comprising:
a first anchor screw assembly comprising a first passage and a first screw, the first screw having a threaded portion configured to be screwed into a first vertebra;
a second anchor screw assembly comprising a second passage and a second screw, the second screw having a threaded portion configured to be screwed into a second vertebra adjacent the first vertebra;
an elongate member receivable in the first and second passages for stabilizing the first and second vertebra with respect to each other, the elongate member comprising an exposed portion extending between the first and second anchor screw assemblies; and
a spacer securable to the exposed portion of the elongate member, the spacer having a length substantially similar to a length of the exposed portion of the elongate member for preventing the first and second anchor screw assemblies from moving substantially towards one another, wherein the spacer comprises a "C" shaped clip receivable around the elongate member, the clip comprising opposing edges that may be compressed around the elongate member to secure the clip to the elongate member.

9. A spinal fixation system, comprising:
a first anchor screw assembly comprising a first passage and a first screw, the first screw having a threaded portion configured to be screwed into a first vertebra, wherein the first screw comprises a head portion opposite the threaded portion comprising a shoulder, and wherein the first anchor screw assembly further comprises a swing bolt pivotally coupled to a second portion of the screw, and a clamp assembly on the swing bolt comprising the first passage therethrough, the clamp assembly comprising first and second clamp portions, the first and second clamp portions having cooperating grooves therein together defining the first passage when the first and second clamp portions are received on the swing bolt;
a second anchor screw assembly comprising a second passage and a second screw, the second screw having a threaded portion configured to be screwed into a second vertebra adjacent the first vertebra;
an elongate member receivable in the first and second passages, the elongate member comprising an exposed portion extending between the first and second anchor screw assemblies; and
a spacer securable to the exposed portion of the elongate member, the spacer having a length substantially similar to a length of the exposed portion of the elongate member for preventing the first and second anchor screw assemblies from moving substantially towards one another.

10. The spinal fixation system of claim 9, wherein the shoulder is radiused, and wherein the first clamp portion comprises a recess adjacent a lower surface of the first clamp portion that intersects the first passage, the recess having a radiused shape for pivotally receiving the shoulder therein before the clamp assembly is fully secured on the swing bolt.

11. A method for stabilizing vertebrae of a patient relative to one another, the method comprising:

screwing a first anchor screw assembly into a first vertebra;

screwing a second anchor screw assembly into a second vertebra adjacent the first vertebra;

securing an elongate member to the first and second anchor screws assemblies, thereby fixing a relative spacing of the first and second vertebrae; and securing a "C" shaped spacer to the elongate member, the spacer extending substantially between the first and the second anchor screws to prevent the first and second anchor screws from moving towards one another after the patient returns to an active vertical position.

12. The method of claim 11, wherein the step of securing the spacer involves increasing a distance between the first and second vertebrae before securing the spacer to the elongate member.

13. The method of claim 11, wherein the step of securing the elongate member comprises:

attaching a first clamp assembly to the first anchor screw assembly;

attaching a second clamp assembly to the second anchor screw assembly; and securing the elongate member to the first and second clamp assemblies.

14. The method of claim 11, further comprising bending the elongate member to conform to a natural curvature of the vertebrae.

15. The method of claim 11, further comprising:

screwing a third anchor screw into a third vertebra adjacent the first second vertebra;

securing the elongate member to the third anchor screw; and securing a spacer to the elongate member between the second and the third anchor screws to prevent the second and third anchor from moving towards one another.

16. A method for stabilizing vertebrae relative to one another, the method comprising:

screwing a first anchor screw into a first vertebra;

screwing a second anchor screw into a second vertebra adjacent the first vertebra;

securing an elongate member to the first and second anchor screws, thereby fixing a relative spacing of the first and second vertebrae; and securing a spacer to the elongate member, the spacer extending substantially between the first and the second anchor screws to prevent the first and second anchor from moving towards one another, and the spacer comprises a "C" shaped clip, and wherein the step securing a spacer comprises crimping the spacer around at least a portion of the elongate member.

17. A method for stabilizing vertebrae relative to one another, the method comprising:

screwing a first anchor screw into a first vertebra;

screwing a second anchor screw into a second vertebra adjacent the first vertebra;

securing an elongate member to the first and second anchor screws, thereby fixing a relative spacing of the first and second vertebrae; and securing a spacer to the elongate member, the spacer extending substantially between the first and the second anchor screws to prevent the first and second anchor from moving towards one another, wherein each of the first and second anchor screws comprise a swing bolt pivotally coupled to a threaded portion, the method comprising adjusting an angle of one or more of the swing bolts on the first and second anchor screws about respective pivot axes to adjust alignment of the first and second anchor screws relative to one another.

18. A kit for stabilizing vertebrae relative to one another, comprising:

one or more substantially rigid rods for enabling the vertebrae to be stabilized relative one another, a plurality of "C" shaped spacers having a plurality of lengths, the spacers comprising opposing edges defining a pocket therebetween for receiving the one or more rods therein; and a plurality of anchor screw assemblies, the anchor screw assemblies comprising anchor screws and a plurality of clamp assemblies for receiving the one or more rods therein.

19. The kit of claim 18, further comprising a crimping tool for crimping at least a portion of the opposing edges of the spacers around the one or more rods to secure the spacers to the rods.

20. The kit of claim 18, further comprising an apparatus for bending the one or more rods to conform to a natural curvature of a patient's spinal column.

21. The kit of claim 18, wherein the plurality of clamp assemblies comprise a plurality of upper and lower clamp portions that may be mated together to define a passage for receiving one of the one or more rods therein, the upper and lower clamp portions comprising a plurality of lengths and passage configurations.

* * * * *